US011744979B2

(12) United States Patent
Foote et al.

(10) Patent No.: US 11,744,979 B2
(45) Date of Patent: Sep. 5, 2023

(54) HUMIDIFIER

(71) Applicant: ResMed Pty Ltd, Bella Vista (AU)

(72) Inventors: Roger Mervin Lloyd Foote, Sydney (AU); Ronald James Huby, Sydney (AU); Andrew Roderick Bath, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 887 days.

(21) Appl. No.: 16/390,808

(22) Filed: Apr. 22, 2019

(65) Prior Publication Data
US 2019/0247608 A1 Aug. 15, 2019

Related U.S. Application Data

(63) Continuation of application No. 13/980,196, filed as application No. PCT/AU2012/000056 on Jan. 24, 2012, now Pat. No. 10,307,559.

(30) Foreign Application Priority Data

Jan. 24, 2011 (AU) .............................. 2011900214
May 20, 2011 (AU) .............................. 2011901960

(51) Int. Cl.
*A61M 16/16* (2006.01)
*A61M 16/14* (2006.01)
(Continued)

(52) U.S. Cl.
CPC .............. *A61M 16/16* (2013.01); *A61L 9/00* (2013.01); *A61M 16/024* (2017.08);
(Continued)

(58) Field of Classification Search
CPC ............ A61M 16/024; A61M 16/0833; A61M 16/0841; A61M 16/10; A61M 16/1045;
(Continued)

(56) References Cited

U.S. PATENT DOCUMENTS 2,699,927 A 1/1955 Gilroy
2,775,962 A 1/1957 Sontag
(Continued)

FOREIGN PATENT DOCUMENTS

CN 1370085 A 9/2002
CN 1491525 A 4/2004
(Continued)

OTHER PUBLICATIONS

Office Action dated Aug. 10, 2021 issued in Japanese Application No. 2020-127380 with English translation (7 pages).
(Continued)

*Primary Examiner* — Annette Dixon
(74) *Attorney, Agent, or Firm* — Nixon & Vanderhye P.C.

(57) ABSTRACT

A humidifier includes a heating element including a porous structure of electrically resistive and thermally conductive material configured to substantially vaporise liquid that is passed through the porous structure. The porous structure has a liquid inlet and a vapour outlet. The humidifier further includes an outer housing surrounding at least a portion of the porous structure for containing the liquid and vapour within the porous structure. The porous structure includes a first electrical connector and a second electrical connector, the first and second connectors being configured for receiving electrical power and applying a voltage across the porous structure to generate heat.

34 Claims, 13 Drawing Sheets

(51) Int. Cl.
　　　*A61M 16/10*　　(2006.01)
　　　*H05B 3/42*　　(2006.01)
　　　*A61M 16/08*　　(2006.01)
　　　*A61M 16/00*　　(2006.01)
　　　*A61L 9/00*　　(2006.01)

(52) U.S. Cl.
　　　CPC ...... *A61M 16/0833* (2014.02); *A61M 16/109* (2014.02); *A61M 16/1075* (2013.01); *A61M 16/1095* (2014.02); *A61M 16/142* (2014.02); *A61M 16/161* (2014.02); *H05B 3/42* (2013.01); *A61M 16/162* (2013.01); *A61M 2016/0024* (2013.01); *A61M 2016/0027* (2013.01); *A61M 2016/0036* (2013.01); *A61M 2205/3368* (2013.01); *A61M 2205/3653* (2013.01); *A61M 2205/50* (2013.01); *A61M 2205/702* (2013.01); *F04C 2270/041* (2013.01); *H05B 2203/021* (2013.01); *H05B 2203/022* (2013.01)

(58) Field of Classification Search
　　　CPC .......... A61M 16/1075; A61M 16/109; A61M 16/1095; A61M 16/145; A61M 16/147; A61M 16/16; A61M 16/161; A61M 16/162; A61M 16/164; A61M 2016/0039; A61M 2205/3368; A61M 2205/3653; A61M 2206/14; B01F 23/21; B01F 35/2135; B01F 35/82; F24F 11/30; F24F 2110/20; F24F 6/14; G05D 22/02; Y02B 30/54; Y10S 261/65

See application file for complete search history.

(56) References Cited

U.S. PATENT DOCUMENTS

| | | | |
|---|---|---|---|
| 2,981,526 | A | 4/1961 | Grumbach |
| 3,826,895 | A | 7/1974 | Schladitz |
| 3,934,117 | A * | 1/1976 | Schladitz ................ H05B 3/48 |
| | | | 338/205 |
| 4,019,021 | A | 4/1977 | Schladitz |
| 4,026,285 | A | 5/1977 | Jackson |
| 4,038,980 | A | 8/1977 | Fodor |
| 4,200,093 | A | 4/1980 | Camp |
| 4,319,566 | A | 3/1982 | Hayward et al. |
| 4,355,636 | A | 10/1982 | Oetjen et al. |
| 4,621,632 | A | 11/1986 | Bartels et al. |
| 4,676,237 | A | 6/1987 | Wood et al. |
| 4,748,314 | A | 5/1988 | Desage |
| 5,148,801 | A | 9/1992 | Douwens et al. |
| 5,318,731 | A | 6/1994 | Yokoya et al. |
| 5,336,156 | A | 8/1994 | Miller et al. |
| 5,346,128 | A * | 9/1994 | Wacker .................. G05D 22/02 |
| | | | 236/44 A |
| 5,349,946 | A * | 9/1994 | McComb .......... A61M 16/1075 |
| | | | 128/203.12 |
| 5,505,911 | A | 4/1996 | Hafele |
| 5,509,405 | A | 4/1996 | Mashak |
| 5,624,610 | A | 4/1997 | Yokoya et al. |
| 5,743,251 | A | 4/1998 | Howell et al. |
| 5,769,071 | A * | 6/1998 | Turnbull ............... A61M 16/16 |
| | | | 128/203.12 |
| 5,906,202 | A | 5/1999 | Schuster et al. |
| 5,916,493 | A | 6/1999 | Miller |
| 6,008,482 | A | 12/1999 | Takahashi |
| 6,078,730 | A | 6/2000 | Huddart et al. |
| 6,095,505 | A * | 8/2000 | Miller ............... A61M 16/1075 |
| | | | 128/203.27 |
| 6,102,037 | A | 8/2000 | Koch |
| 6,394,084 | B1 * | 5/2002 | Nitta .................. A61M 16/161 |
| | | | 128/201.13 |
| 6,397,841 | B1 | 6/2002 | Kenyon |
| 6,510,848 | B1 | 1/2003 | Gibertoni |
| 6,766,220 | B2 * | 7/2004 | McRae ................ A61M 11/042 |
| | | | 700/282 |
| 7,858,247 | B2 | 12/2010 | Kim |
| 7,938,113 | B2 | 5/2011 | Weinstein et al. |
| 8,632,919 | B2 | 1/2014 | Kang |
| 8,733,349 | B2 | 5/2014 | Bath et al. |
| 2002/0079309 | A1 | 6/2002 | Cox et al. |
| 2004/0016430 | A1 * | 1/2004 | Makinson ........... A61M 16/109 |
| | | | 128/203.12 |
| 2004/0020487 | A1 | 2/2004 | Koch et al. |
| 2004/0102731 | A1 | 5/2004 | Blackhurst et al. |
| 2004/0250815 | A1 | 12/2004 | Scott et al. |
| 2006/0012057 | A1 | 1/2006 | Anthony |
| 2006/0144395 | A1 | 7/2006 | Koch et al. |
| 2006/0283447 | A1 | 12/2006 | Dhuper |
| 2007/0107879 | A1 | 5/2007 | Radomski et al. |
| 2008/0105257 | A1 | 5/2008 | Klasek et al. |
| 2009/0036001 | A1 | 2/2009 | Ishigami |
| 2009/0223514 | A1 | 9/2009 | Smith et al. |
| 2009/0032840 | A1 | 12/2009 | Klasek et al. |
| 2010/0024816 | A1 | 2/2010 | Weinstein et al. |
| 2010/0147299 | A1 | 6/2010 | Row et al. |
| 2010/0319697 | A1 | 12/2010 | Farrugia et al. |
| 2011/0023874 | A1 | 2/2011 | Bath et al. |
| 2011/0108031 | A1 | 5/2011 | Korneff et al. |
| 2012/0017905 | A1 | 1/2012 | Sata et al. |
| 2012/0032359 | A1 | 2/2012 | Jung et al. |

FOREIGN PATENT DOCUMENTS

| | | |
|---|---|---|
| CN | 1623612 A | 6/2005 |
| CN | 1821180 | 8/2006 |
| CN | 1930332 | 3/2007 |
| CN | 101516430 A | 8/2009 |
| CN | 101641130 A | 2/2010 |
| CN | 101868277 A | 10/2010 |
| DE | 27 02 674 | 7/1978 |
| DE | 41 16 512 | 11/1992 |
| DE | 43 03 645 | 8/1994 |
| DE | 43 12 793 | 10/1994 |
| EP | 0 716 861 | 6/1996 |
| EP | 1 075 849 | 2/2001 |
| EP | 2 269 680 B1 | 9/2012 |
| GB | 2 136 705 | 9/1984 |
| JP | 49-128337 | 12/1974 |
| JP | 4-340041 | 11/1992 |
| JP | 10-28737 | 2/1998 |
| JP | 2005-024176 A | 1/2005 |
| JP | 2005-503220 A | 2/2005 |
| JP | 2006-162167 A | 6/2006 |
| JP | 2009-523035 | 6/2009 |
| JP | 2009-213888 | 9/2009 |
| JP | 2012-513236 | 6/2012 |
| WO | 96/13138 A1 | 5/1996 |
| WO | 01/13981 A1 | 3/2001 |
| WO | 2007/101298 A1 | 9/2007 |
| WO | 2008/024001 | 2/2008 |
| WO | 2008055308 | 5/2008 |
| WO | 2009015410 | 2/2009 |
| WO | 2009022004 | 2/2009 |
| WO | 2010/028427 A1 | 3/2010 |
| WO | 2010/073160 | 7/2010 |
| WO | WO 2010/073160 | 7/2010 |
| WO | WO 2010/073160 A1 | 7/2010 |
| WO | 2010/116847 | 10/2010 |
| WO | 2012077052 | 6/2012 |
| WO | 2012080923 | 6/2012 |
| WO | 2012080941 | 6/2012 |
| WO | 2010/116847 | 10/2012 |
| WO | 2015135040 | 9/2015 |

OTHER PUBLICATIONS

Office Action dated Oct. 14, 2021 issued in Chinese Application No. 201910380473.1 with English translation (17 pages).
Examination Report dated Jun. 4, 2019 issued in European Application No. 12739490.6 (4 pages).

(56) References Cited

OTHER PUBLICATIONS

Office Action dated Jul. 31, 2019 issued in Chinese Application No. 201710087480.3 with English translation (9 pages).
Amended Statement of Case dated Jan. 31, 2020, filed by Fisher & Paykel Healthcare Limited in New Zealand Application No. 705158 Showing Markups (27 pages).
Amended Statement of Case dated Jan. 31, 2020, filed by Fisher & Paykel Healthcare Limited in New Zealand Application No. 705158 No Markups (27 pages).
Office Action dated Feb. 25, 2020 issued in Chinese Application No. 201710087480.3 with English translation (12 pages).
Office Action dated Apr. 27, 2021 issued in Chinese Application No. 201910380473.1 with English translation (19 pages).
Dec. 19, 2018 First Office Action issued in Chinese Application No. 201710087480.3 (with translation).
Notice of Allowance dated Jul. 30, 2018 issued in Japanese Application No. 2016-082696 with English translation (6 pages).
Notice of Reasons for Rejection dated Jan. 15, 2018 issued in Japanese Application No. 2016-082696 with English translation (9 pages).
Notice of Reasons for Rejection dated Dec. 25, 2017 issued in Japanese Application No. 2013-549676 with English translation (20 pages).
Communication Regarding Deadline for Counterstatement dated Mar. 8, 2017 issued in New Zealand Application No. 705158 (2 pages).
First Amended Notice of Opposition (Marked Up) filed by Fisher & Paykel Healthcare Limited (2 pages).
First Amended Notice of Opposition (Clean) filed by Fisher & Paykel Healthcare Limited (2 pages).
Statement of Case dated Feb. 27, 2017 filed by Fisher & Paykel Healthcare Limited (26 pages).
Branson RRT, Richard D., et al., "Comparison of Conventional Heated Humidification with a New Active Hygroscopic Heat and Moisture Exchanger in Mechanically Ventilated Patients", Respiratory Care, vol. 44, No. 8, Aug. 1999, pp. 912-917.
Hudson RCI, "Gibeck Humid-Heat" user manual, 2002 (44 pages).
Notice of Reasons for Rejection dated Mar. 17, 2017 issued in Japanese Application No. 2016-82696 with English translation (13 pages).
First Amended Notice of Opposition to Grant of Patent without Mark Ups dated Feb. 21, 2017 filed by Fisher & Paykel Healthcare Limited in New Zealand Application No. 705158 (2 pages).
First Amended Notice of Opposition to Grant of Patent with Mark Ups dated Feb. 21, 2017 filed by Fisher & Paykel Healthcare Limited in New Zealand Application No. 705158 (2 pages).
Statement of Case dated Feb. 27, 2017 filed by Fisher & Paykel Healthcare Limited in New Zealand Application No. 705158 (26 pages).
Branson, Richard D., RRT, et al., "Comparison of Conventional Heated Humidification with a New Active Hygroscopic Heat and Moisture Exchanger in Mechanically Ventilated Patients", Respiratory Care, vol. 44, No. 8, Aug. 1999 (7 pages).
Gibeck Humid-Heat® Aktiver Atemgasbefeuchter Gebrauchanweisung, Hudson RCI, Manual, undated (44 pages).
Notice of Opposition to Grant of Patent dated Dec. 22, 2016 filed by Fisher & Paykel Healthcare Limited in New Zealand Application No. 705158 (2 pages).
Extension of Time Granted dated Dec. 22, 2016 issued by New Zealand Intellectual Property Office in New Zealand Application No. 705158 (1 page).
Decision of Rejection dated Sep. 12, 2016 issued in Japanese Application No. 2013-549676 with English translation (11 pages).
Patent Examination Report No. 1 dated Sep. 1, 2016 issued in Australian Application No. 2015204372 (5 pages).
Notice of Reasons for Rejection dated Jan. 18, 2016 issued in Japanese Application No. 2013-549676 with English language translation (8 pages).
Notification of Second Office Action issued in Chinese Application No. 201280006394.0 with English translation (11 pages).
First Examination Report dated Mar. 9, 2015 issued in New Zealand Application No. 705158 (3 pages).
Notification of First Office Action dated Jul. 15, 2015 issued in Chinese Application No. 201280006394.0 with English translation (25 pages).
First Examination Report dated Jul. 4, 2014 issued in corresponding Australian Application No. 2012211031 (4 pages).
First Examination Report dated Feb. 25, 2014 in New Zealand Application No. 613110 (3 pages).
International Search Report for PCT/AU2012/000056 dated Apr. 13, 2012.
V. Oyj, "Humidity Conversion Formulas Calculation Formulas as Humidity" Helsinki, 2011, pp. 1-16.
Office Action dated Sep. 9, 2020 issued in Chinese Application No. 201710087480.3 with English translation (7 pages).
Proceeding Correspondence dated Sep. 30, 2020 issued in New Zealand Application No. 705158 (3 pages).
Office Action dated Oct. 15, 2019 issued in Japanese Application No. 2018-93790 with English translation (17 pages).
Extended European Search Report dated Jan. 25, 2022 issued in European Application No. 21175711.7 (8 pages).
Office Action dated Feb. 15, 2022 issued in Chinese Application No. 201910380473.1 with English translation (8 pages).
Office Action dated Mar. 14, 2022 issued in Japanese Application No. 2020-127380 with English translation (6 pages).
Pre-Appeal Exam Report dated Sep. 1, 2022 issued in Japanese Application No. 2020-127380 with English translation (3 pages).
Notification of Grant dated May 17, 2022 issued in Chinese Application No. 201910380473.1 (4 pages).

\* cited by examiner

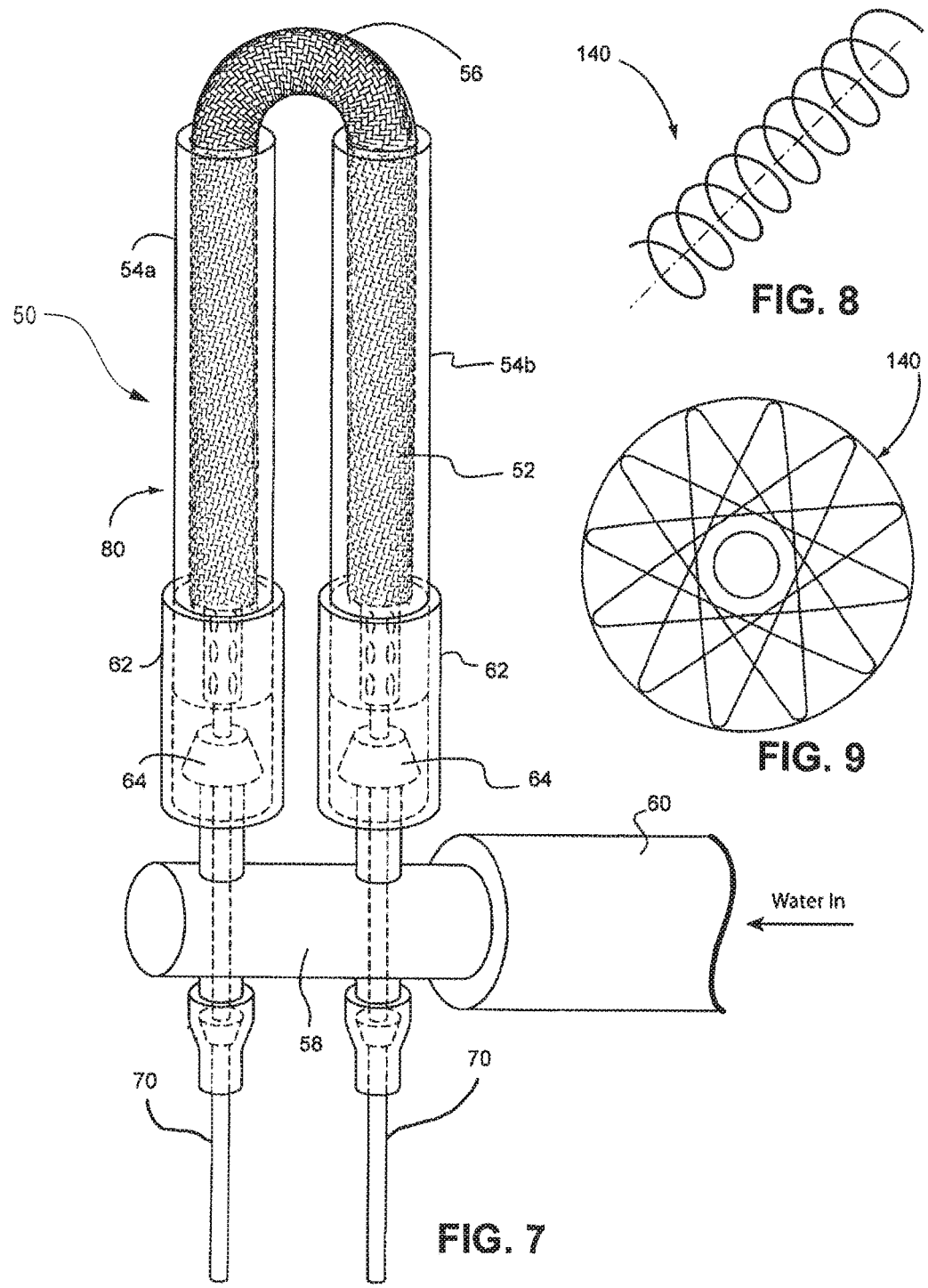

HUMIDIFIER

CROSS REFERENCE TO RELATED APPLICATIONS

This application is a continuation of U.S. application Ser. No. 13/980,196, filed Jul. 17, 2013, now allowed, which is the U.S. national phase of International Application No. PCT/AU2012/00056, filed 24 Jan. 2012 which designated the U.S. and claims priority to AU 2011900214, filed 24 Jan. 2011, and AU 2011901960, filed 20 May 2011, the entire contents of each of which are hereby incorporated by reference.

FIELD OF THE TECHNOLOGY

The present technology relates to a humidifier and method for use in patient ventilation, e.g., for treatment of Sleep Disordered Breathing (SDB) with Continuous Positive Airway Pressure (CPAP) or Non-Invasive Positive Pressure Ventilation (NIPPV), or treatment of other respiratory disorders.

BACKGROUND OF THE TECHNOLOGY

CPAP treatment of SDB involves the delivery of a pressurised breathable gas, usually air, to a patient's airways using a conduit and mask. Gas pressures employed for CPAP typically range from 4 cm $H_2O$ to 28 cm $H_2O$, at flow rates of up to 180 L/min (measured at the mask), depending on patient requirements. The pressurised gas acts as a pneumatic splint for the patient's airway, preventing airway collapse, especially during the inspiratory phase of respiration.

CPAP apparatus comprises a flow generator or blower for supplying pressurised respiratory gas, such as air, to the patient via an air delivery tube leading to a patient interface, such as a nasal or oronasal mask, or nasal cushion or nasal pillows arrangement.

CPAP machines are known which incorporate humidifying devices, either separately from the flow generator or integrated therewith. An example of a flow generator/humidifier unit is the ResMed® S9 with H5i humidifier sold by the present Applicant. The volume of such humidifiers is relatively large due to the requirement of a large surface area to heat the water supply, for example an approximate volume of 1680000 $mm^3$ (1,680 ml).

Humidification of the air supply is typically carried out by passing the air exiting the flow generator over the surface of a body of water in a heated water reservoir. However, such humidifiers are cumbersome and may be prone to spillage, and are relatively slow to activate and to adjust humidification level.

SUMMARY OF THE TECHNOLOGY

One aspect of the present technology relates to a humidifier. The present technology also relates to a method which is suitable for humidification of respiratory gases for patient treatment, e.g. of respiratory disorders. The humidification apparatus and method are configured to provide a rapid vaporisation of liquid for supply to the respiratory gases.

Another aspect of the present technology relates to a humidifier having a small volume of liquid for vaporisation for supply to respiratory gases for patient treatment. In certain examples the volume of the humidifier is between approximately 19000 $mm^3$ (19 ml) and 190000 $mm^3$ (190 ml). Thus, the humidifier may be 20%, such as approximately 1-12%, smaller than current humidifiers by volume.

A further aspect of the present technology relates to a humidifier that vaporises water at a slow rate, for example 0-10 ml/min, preferably 0-6 ml/min, more preferably 0-1.5 ml/min.

A further aspect of the present technology relates to a humidifier that vaporises a small volume of water, for example 0-10 ml, preferably 0-6 ml, more preferably 0-1.5 ml.

In certain examples the volume of water is controlled to control the humidification level delivered by the humidifier. In some examples, the power to vaporise the water is controlled to control the humidification level delivered by the humidifier.

Yet another aspect of the present technology relates to a humidifier component comprising a porous structure of thermally conductive material configured to act as a heating element to substantially vaporise liquid, for example water that is passed therethrough. In certain examples, the porous structure is an electrically conductive material such as metal foam, through which both electric current and water are passed so that the porous structure acts as a resistance heater to vaporise at least part of the water within it.

A still further aspect of the present technology relates to a humidifier comprising: a water supply, an electrical power supply, and a porous structure of thermally conductive material having a water inlet in communication with the water supply and a vapour outlet in communication with a gas stream to be humidified, the porous structure being connected to the electrical power supply such that the porous structure acts as a heater to vaporise water within the porous structure as it travels towards the vapour outlet. In certain examples the humidifier is a humidifier for respiratory gases.

Another aspect of the present technology relates to a humidifier comprising a water supply, a means for supplying a volume of water, and a steam generator, wherein the supply means is configured to supply a volume of water from the water supply as required to the steam generator, the steam generator substantially converts the volume of water into steam and the steam is supplied into a respiratory gas flow path for delivery to a patient. The steam generator may comprise a porous structure of thermally conductive material though which the supply of water is passed through.

In certain examples, the porous structure comprises a body of open pore metal foam or other electrically resistive and/or thermally conductive material. A porous structure is to be considered any structure having a plurality of pores that allows fluid to pass therethrough. Example pore size may be from about 0.1 to 2 mm pore diameter, for example from about 0.2 to 1.0 mm, and such as about 0.4 mm.

Example metals for the foam include super alloys such as chromium alloys. Example chromium alloys include MCrAlX, where M is one or more of Nickel (Ni), Cobalt (Co) or Iron (Fe) contributing at least about 50% by weight, Chromium (Cr) contributing between 8% and 35% by weight, Aluminium (Al) contributing greater than 0% but less than about 8% by weight, and X contributing less than about 25% by weight, with X consisting of zero or more other elements, including but not limited to Molybdenum (Mo), Rhenium (Re), Ruthenium (Ru), Titanium (Ti), Tantalum (Ta), Vanadium (V), Tungsten (W), Niobium (Nb), Zirconium (Zr), Boron (B), Carbon (C), Silicon (Si), Yttrium (Y) and Hafnium (Hf). Another example chromium alloy is a nickel-chromium alloy or Inconel® alloys. Other suitable materials may include porous ceramic materials such as silicon carbide, titanium nitride, or carbon such as pyrolytic carbon.

According to still another aspect of the present technology, the porous structured steam generator may comprise fibrous materials which are electrically resistive and/or thermally conductive. The body of fibres may preferably be bundled in groups forming tow-, twist-, knit-, braid-, felt-, woven fabric- or tape-structures. The bundled fibrous structure having a plurality of apertures, or pores, which allow fluid to pass therethrough. Examples of fibrous materials include carbon fibres having a carbon content of greater than about 50% and having precursors of Poly Acrylic Nitrile (PAN), rayon or pitch. The carbon fibre diameters may be less than 20 microns, for example about 5 to 7 microns.

Still another aspect of the present technology relates to a humidifier that includes a tube surrounding at least a portion of the porous structure for containing water and water vapour within the porous structure. The porous structure and the tube may each be elongate, and a vapour outlet end of the porous structure may be exposed to the gas stream to be humidified through an open end of the tube. In one example, the vapour outlet end of the porous structure extends beyond the surrounding tube.

A still further aspect of the present technology relates to a humidifier adapted for mounting within an air delivery tube, and the arrangement further includes a mounting structure for mounting the humidifier within the air delivery tube. The mounting structure may be adapted to space the humidifier from the internal walls of the air delivery tube. The mounting structure may support and locate the humidifier within a central location within the air delivery tube. In certain examples the mounting structure may include a coil structure, such as a "porcupine" coil structure, adapted to mount the humidifier substantially parallel to the longitudinal axis of the air delivery tube.

According to one example of the present technology, a humidifier comprises a heating element including a porous structure of electrically resistive and thermally conductive material configured to substantially vaporise liquid that is passed through the porous structure, the porous structure having a liquid inlet and a vapour outlet; an outer tube surrounding at least a portion of the porous structure for containing the liquid and vapour within the porous structure; a first power lead connected to the liquid inlet by a first electrical connector; and a second power lead connected to the vapour outlet by a second electrical connector, wherein the first power lead and the second power lead are configured to apply a voltage across the porous structure.

Another aspect of the present technology relates to a respiratory device and method comprising an air heater coil adapted to heat the air flow. Preferably the air heater coil is configured to cover substantially all or most of the air flow path. The air coil heater may be located in a flow generator, humidifier, patient interface, air delivery tube and/or at any connection point between such devices.

According to a further aspect of the present technology, an air heater coil comprising a plurality of offset or overlapping loops or "petals" to form a rosette configuration structured to cover substantially all or most of the cross-sectional area of an air flow path to ensure the air flow is in close proximity to at least part of the heating wires at some stage of its flow.

According to another example of the present technology, a respiratory apparatus for delivering a flow of breathable gas to a patient comprises a flow generator configured to generate the flow of breathable gas; and a humidifier according to the present technology.

Another aspect of some forms of the present technology relates to a method of treating a respiratory disorder with humidified air. Another aspect of some forms of the present technology relates to a method of humidifying air. Another aspect of some forms of the present technology relates to a method of operating a humidifier component. Another aspect of some forms of the present technology relates to a method of operating a humidifier.

Further aspects and examples of the present technology will be apparent from the following description, and the appended claims. Further aspects are described below.

According to aspect 1, a humidifier comprises a heating element including a porous structure of electrically resistive and thermally conductive material configured to substantially vaporise liquid that is passed through the porous structure, the porous structure having a liquid inlet and a vapour outlet; an outer tube surrounding at least a portion of the porous structure for containing the liquid and vapour within the porous structure; a first power lead connected to the liquid inlet by a first electrical connector; and a second power lead connected to the vapour outlet by a second electrical connector, wherein the first power lead and the second power lead are configured to apply a voltage across the porous structure.

2. A humidifier according to aspect 1, further comprising a connector configured to deliver liquid from a supply of liquid to the liquid inlet.

3. A humidifier according to aspect 2, wherein the connector comprises a connection spigot, and the humidifier further comprises a sealing tube configured to form a sealed connection between the connection spigot and the outer tube.

4. A humidifier according to aspect 2 or aspect 3, wherein the connector comprises a liquid inlet spigot configured to receive liquid from a liquid supply.

5. A humidifier according to aspect 4, further comprising a liquid supply tube connected to the liquid inlet spigot.

6. A humidifier according to any one of aspects 2-5, wherein the connector comprises a sealing connector configured to seal the first power lead passing through the connector to the liquid inlet.

7. A humidifier according to any one of aspects 1-6, wherein the first electrical connector is a crimp connector.

8. A humidifier according to any one of aspects 1-7, wherein the porous structure and the outer tube are each elongate, and the vapour outlet of the porous structure is configured to be exposed to a flow of breathable gas to be humidified through an open end of the outer tube.

9. A humidifier according to aspect 8, wherein the vapour outlet of the porous structure extends beyond the surrounding tube.

10. A humidifier according to aspect 8 or aspect 9, wherein the second electrical connector is a crimp connector.

11. A humidifier according to any one of aspects 1-10, wherein the porous structure has a cylindrical shape.

12. A humidifier according to any one of aspects 1-10, wherein the porous structure has a tapered shape.

13. A humidifier according to aspect 12, wherein the porous structure has a larger diameter at the vapour outlet than at the liquid inlet.

14. A humidifier according to any one of aspects 1-13, wherein the porous structure is formed of an open pore metal foam.

15. A humidifier according to aspect 14, wherein the metal comprises a chromium alloy.

16. A humidifier according to aspect 15, wherein the chromium alloy comprises MCrAlX, where M is one or more of Nickel (Ni), Cobalt (Co) or Iron (Fe) contributing at least 50% by weight, Chromium (Cr) contributing between about 8% and 35% by weight, Aluminium (Al) contributing greater than 0% but less than about 8% by weight, and X contributing less than about 25% by weight, with X including zero or more other elements, including to Molybdenum (Mo), Rhenium (Re), Ruthenium (Ru), Titanium (Ti), Tantalum (Ta), Vanadium (V), Tungsten (W), Niobium (Nb), Zirconium (Zr), Boron (B), Carbon (C), Silicon (Si), Yttrium (Y) and Hafnium (Hf).

17. A humidifier according to any one of aspects 14-16, wherein the metal foam is formed by pyrolysis and/or metallisation of a polymer foam such as an open cell polyurethane foam.

18. A humidifier according to any one of aspects 14-17, wherein the metal foam has an open pore volume of 90% or greater, for example about 95%.

19. A humidifier according to any one of aspects 14-18, wherein a pore size of the metal foam is about 0.1 to 2 mm, for example about 0.2 to 1 mm, such as about 0.4 mm.

20. A humidifier according to any one of aspects 1-13, wherein the porous structure comprises a body of fibres.

21. A humidifier according to aspect 20, wherein the body of fibres is bundled in a form of tow filaments, twist, knit, braid, woven fabric or tape structures.

22. A humidifier according to aspect 20 or 21, wherein the body of fibres comprises carbon fibres having a carbon content of greater than about 50%.

23. A humidifier according to aspect 22, wherein the carbon fibers have precursors of Poly Acyrlic Nitrile, rayon and/or pitch.

24. A humidifier according to aspect 22 or aspect 23, wherein the carbon fibers have a diameter of less than about 20 microns, for example about 5 to 7 microns.

25. A humidifier according to any one of aspects 1-13, wherein the porous structure is formed of ceramic material such as silicon carbide, titanium nitride or pyrolytic carbon.

26. A humidifier according to any one of aspects 1-25, wherein the porous structure has a substantially uniform porosity.

27. A humidifier according to any one of aspects 1-25, wherein the porous structure has a varying porosity along its length and/or diameter.

28. A humidifier according to any one of aspects 1-27, wherein the porous structure has a diameter of between about 1 to 5 mm, for example about 2 mm.

29. A humidifier according to any one of aspects 1-28, wherein the porous structure has a length of between about 20 to 200 mm, for example about 100 mm.

30. A humidifier according to any one of aspects 1-29, wherein the porous structure has a volume of between about 10 to 4000 mm$^3$, for example about 15 to 500 mm$^3$, such as about 314 mm$^3$.

31. A humidifier according to any one of aspects 1-30, wherein the outer tube is formed of electrically and thermally insulating material.

32. A humidifier according to aspect 31, wherein the outer tube is formed of alumina or fused quartz.

33. A humidifier according to aspect 31, wherein the outer tube is formed of a polymer, such as heat shrink or silicone rubber.

34. A humidifier according to any one of aspects 1-33, further comprising an air delivery tube and a mounting structure for mounting the humidifier within the air delivery tube.

35. A humidifier according to aspect 34, wherein, the mounting structure is adapted to space the humidifier from an internal wall of the air delivery tube.

36. A humidifier according to aspect 34 or aspect 35, wherein, the mounting structure includes a coil structure adapted to mount the humidifier substantially parallel to the longitudinal axis of the air delivery tube.

37. A humidifier according to aspect 15, wherein the coil structure comprises a resistant heater configured to heat air flowing through the air delivery tube.

38. A humidifier according to any one of aspect 1-37, further comprising a liquid supply configured to supply liquid to the liquid inlet.

39. A humidifier according to aspect 38, wherein the liquid supply comprises a micro-pump or a piezo electric pump.

40. A humidifier according to aspect 38, wherein the liquid supply comprises a gravity feed.

41. A humidifier according to any one of aspects 38-40, wherein the liquid supply is configured to deliver about 2-10 ml/min, for example about 2-6 ml/min, such as about 4-5 ml/min of liquid.

42. A humidifier according to any one of aspects 38-41, wherein the liquid supply is configured to supply water.

43. A humidifier according to any one of aspects 1-42, further comprising a power supply configured to supply the voltage across the porous structure.

44. A humidifier according to aspect 43, further comprising a controller configured to control the power supply.

45. A humidifier according to aspect 44, wherein the controller controls the power supply sot that vapour is delivered only during an inspiratory phase of a patient's breathing cycle.

46. A respiratory apparatus for delivering a flow of breathable gas to a patient, comprising:
a flow generator configured to generate the flow of breathable gas; and
a humidifier according to any one of aspects 1-45 configured to humidify the flow of breathable gas.

47. A respiratory apparatus according to aspect 46, wherein the flow generator is configured to generate the flow of breathable gas at a pressure of about 4 to 28 cm $H_2O$.

48. A respiratory apparatus according to aspect 46 or aspect 47, wherein the flow generator is configured to generate a flow of breathable gas of between about 100 to 180 L/min.

49. A respiratory apparatus according to any one of aspects 46-48, further comprising a least one sensor configured to detect a temperature of ambient gas entering the flow generator, a relative humidity of the ambient gas, an absolute humidity of the ambient gas, a temperature of the flow of breathable gas, a temperature of the humidified flow of breathable gas, a relative humidity of the humidified flow of breathable gas, an absolute humidity of the flow of breathable gas, a pressure of the flow of breathable gas, and a rate of the flow of breathable gas.

50. A respiratory apparatus according to aspect 49, further comprising a controller configured to receive a signal from the at least one sensor and configured to control the humidifier to provide the humidified flow of breathable gas at a predetermined temperature and a predetermined relative humidity.

51. A respiratory apparatus according to aspect 50, wherein the controller of the respiratory apparatus is configured to control the flow generator and the power supply of the humidifier.

52. A respiratory apparatus according to any one of aspects 46-51, wherein the humidifier is disposed in a delivery tube between the flow generator and a patient interface configured to seal with the patient's airways.

53. A respiratory apparatus according to any one of aspects 46-51, wherein the humidifier is disposed in a delivery tube between the flow generator and a patient interface configured to seal with the patient's airways.

54. A humidifier comprises: a porous structure of thermally conductive material configured to act as a heating element to substantially vaporise liquid that is passed therethrough.

55. A humidifier according to aspect 54, wherein the porous structure acts as a resistance heater to vaporise at least part of the liquid within it.

56. A humidifier according to aspect 54 or aspect 55, wherein the porous structure is formed of electrically resistive material.

57. A humidifier comprises an electrical power supply; and a porous structure of thermally conductive material having a liquid inlet adapted for communication with a liquid supply and a vapour outlet in communication with a gas stream to be humidified, the porous structure being connected to the electrical power supply such that the porous structure acts as a heater to vaporise liquid within the porous structure as it travels towards the vapour outlet.

58. A humidifier according to any one of aspects 54-57, wherein the humidifier is a humidifier for respiratory gases.

59. A humidifier according to any one of aspects 54-58, wherein the porous structure comprises a body of open pore metal foam or a body of fibres bundled in a form of tow filaments, twist, knit, braid woven fabric or tape structures.

61. A humidifier according to aspect 59 or 60, wherein the body of fibres comprises carbon fibres.

62. A humidifier according to any one of aspects 53-61, wherein the humidifier further includes a tube surrounding at least a portion of the porous structure for containing liquid and vapour within the porous structure.

63. A humidifier according to aspect 62, wherein the porous structure and the tube are each elongate, and a vapour outlet of the porous structure is exposed to a gas stream to be humidified through an open end of the tube.

64. A humidifier according to aspect 62 or aspect 63, wherein the vapour outlet of the porous structure extends beyond the surrounding tube.

65. A humidifier according to any one of aspects 53-64, wherein the humidifier is adapted for mounting within an air delivery tube, and the arrangement further includes a mounting structure for mounting the humidifier within the air delivery tube.

66. A humidifier according to aspect 65, wherein the mounting structure is adapted to space the humidifier from an internal wall of the air delivery tube.

67. A humidifier according to aspect 65 or aspect 66, wherein the mounting structure includes a coil structure adapted to mount the humidifier substantially parallel to the longitudinal axis of the air delivery tube.

68. A humidifier according to aspect 67, wherein the coil structure is further adapted to act as a resistant heater to heat air flowing through the air delivery tube.

69. A humidifier comprising: a supply means; and a steam generator, wherein the supply means is configured to supply a volume of water from a water supply as required to the steam generator, the steam generator substantially converts the volume of water into steam and the steam is supplied into a respiratory gas flow path for delivery to a patient.

70. A humidifier according to aspect 69, wherein the steam generator comprises a porous structure of thermally conductive material through which the supply of water is passed through.

71. A humidifier according to aspect 69, wherein the steam generator comprises a fibrous structure of thermally conductive material through which the supply of water is passed through.

72. A humidifier according to aspect 71, wherein the fibrous structure comprises bundled carbon fibre.

73. A humidifier according to any one of aspects 69-72, wherein the respiratory airflow is preheated.

74. A humidifier according to any one of aspects 69-73, wherein the supply means is a pump configured to pump a volume of water to the steam generator.

75. A humidifier according to any one of aspects 69-74, wherein the steam is delivered only during an inspiratory phase of the patient's breathing cycle.

76. A method of humidifying a flow of breathable gas, comprising: feeding liquid to an inlet of a porous structure of thermally conductive, electrically resistive material; passing electric current through the porous structure to vaporise the liquid; and exposing an outlet of the porous structure to the flow of breathable gas to humidify the flow of breathable gas.

77. A method according to aspect 76, further comprising: sealing the inlet of the porous structure from the flow of breathable gas.

78. A method according to aspect 76 or aspect 77, wherein feeding the liquid comprises pumping the liquid.

79. A method according to aspect 76 or aspect 77, wherein feeding the liquid comprises feeding the liquid by gravity.

80. A method according to any one of aspects 76-79, further comprising: determining at least one of an ambient temperature of gas used to form the flow of breathable gas, a relative humidity of the gas used to form the flow of breathable gas, an absolute humidity of the gas used to form the flow of breathable gas, a pressure of the flow of breathable gas, and/or an amount of the flow of breathable gas; and controlling at least one of the electric current, the feeding of the liquid to the inlet of the porous structure, and/or the volume of the flow of breathable gas to provide at least one of a predetermined relative humidity, absolute humidity, and/or temperature to the humidified flow of breathable gas.

81. A method according to any one of aspects 76-80, further comprising: heating the flow of breathable gas prior to exposing the flow of breathable gas to the outlet of the porous structure.

82. A method according to any one of aspects 76-81, wherein feeding the liquid to the inlet of a porous structure comprises feeding about 2-10 ml/min, for example about 2-6 ml/min, such as about 4-5 ml/min of liquid.

83. A method according to any one of aspects 76-82, wherein passing the electric current through the porous structure comprises applying a voltage between about 12 V to 24 V to the porous structure.

84. A method according to any one of aspects 76-83, wherein exposing the outlet of the porous structure to the flow of breathable gas comprises exposing the outlet to a flow of breathable gas of between about 100 to 180 L/min.

85. A method according to any one of aspects 76-84, wherein exposing the outlet of the porous structure to the flow of breathable gas comprises exposing the outlet to a flow of breathable gas at a pressure of between about 4 cm $H_2O$ to 28 cm $H_2O$.

86. An air heater coil adapted to heat an airflow within a respiratory device comprising a plurality of loops or petal, each loop or petal arranged to overlap an adjacent loop or petal to form a rosette configuration adapted to cover substantially all or most of a cross-sectional area of an air flow path within the respiratory device.

87. An air heater according to aspect 86, wherein the respiratory device includes one or more of the following components: a flow generator, a humidifier, an air delivery tube, a patient interface and/or a connector coupled between such components, and the air heater is located in at least one of the components.

88. An air heater according to any one of aspects 86-87, wherein the plurality of loops or petals are formed of resistive wire.

89. A method of heating the air flow within a respiratory device comprising: inserting the air heater according to any one of aspects 86-88 into a component of the respiratory device and energising the air heater to heat the air heater to a desired temperature.

90. A method of controlling a humidifier to deliver a predetermined level of humidity supplied to a patient interface, the method comprising the steps of: determining the ambient absolute humidity; calculating a required amount of liquid to be added to a flow of breathable gas; calculating an amount of energy required to vapourise the required amount of liquid; controlling a water supply unit to deliver the required amount of liquid to a porous heating element; and energising the porous heating element with the amount of energy to vapourise the required amount of liquid to deliver the required amount of liquid to the flow of breathable gas.

91. A method of treating a respiratory disorder of a patient with a predetermined level of humidity comprising the steps of: providing a supply of air or breathable gas to the patient; determining an air flowrate of respiratory gas to the patient; determining a volume of water required to humidify the supply of air or breathable gas to the predetermined level of humidity; determining the amount of energy required to deliver the required predetermined level of humidity; determining a phase of a respiratory cycle of the patient; heating the volume of water to produce a volume of steam; and delivering the volume of steam to the supply of air or breathable gas to the patient during a portion of the respiratory cycle of the patient.

92. The method of aspect 91 wherein the portion of the respiratory cycle of the patient is the inspiratory phase of the respiratory cycle of the patient.

BRIEF DESCRIPTION OF THE DRAWINGS

Further examples of the present technology will now be described with reference to the accompanying drawings, in which:

FIG. 6b is an end view of the mounting structure of FIG. 6a;

FIG. 6c is a side view of the mounting structure of FIG. 6a;

FIG. 7 is a view of a humidifier according to another aspect of the present technology;

FIG. 8 is a view of a mounting structure;

FIG. 9 is a view of another mounting structure;

DETAILED DESCRIPTION

Figure 1A:
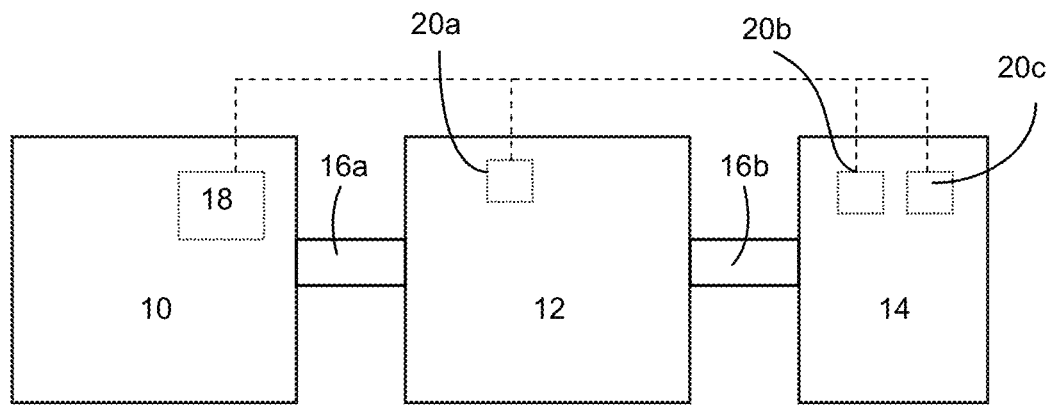
FIGS. 1a to 1c are schematics of examples of a respiratory apparatus incorporating a humidifier according to the present technology.
Figure 1B:
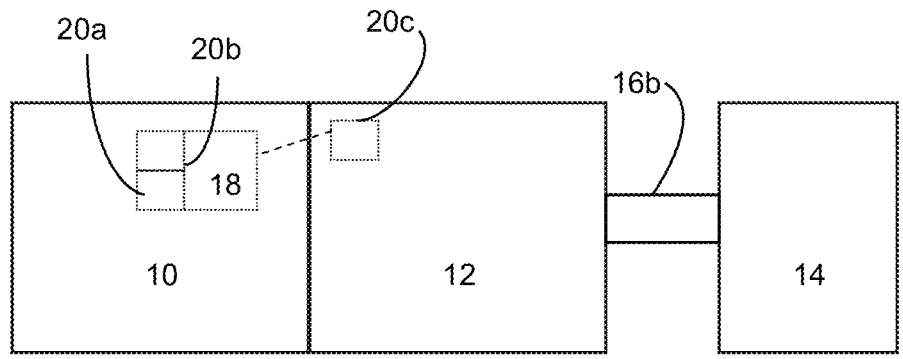
Figure 1C:
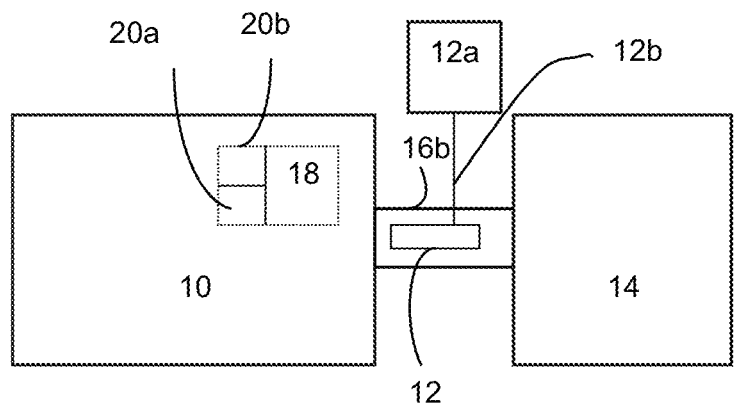

FIG. 1a is a schematic view of a respiratory apparatus including a humidifier according to an example of the present technology. The apparatus comprises a flow generator 10 for generating a supply of air under positive pressure, a humidifier (or humidifier assembly) 12 for increasing humidity of the gas from the flow generator, a patient interface 14 such as a nasal or oronasal mask or nasal cushion or nasal pillows interface, interconnected by air delivery tubes 16a, 16b. Alternatively, the humidifier 12 may be configured to couple directly to an outlet of the flow generator 10 such that interconnecting delivery tube 16a is not required (see FIG. 1b), for example as in the ResMed S9™ PAP system. Furthermore, as illustrated in FIG. 1c and discussed in more detail below, the humidifier 12 may be incorporated within the interconnecting tube 16b. In this arrangement a water supply (or water tub) 12a having a water supply tube 12b is required to provide a source of water (a supply of liquid) to the humidifier 12 located within the air delivery tube 16b. The tubes 16a, 16b may have an internal diameter of, for example, about 10 mm to 22 mm, such as about 15 mm to 22 mm, for example about 12 mm, 13 mm, 14 mm, 15 mm, 19 mm. It should be appreciated that other diameters are possible.

The flow generator 10 may also include a controller 18 for receiving input from a control interface (not shown) of the flow generator and signal/s from one or more sensors 20a, 20b, 20c, for controlling operation of the flow generator 10 and humidifier 12. The sensors 20a, 20b, 20c may be one or more of temperature, pressure, relative humidity, absolute humidity and/or flow sensors, for detecting, for example, a property of ambient, unhumidified flow, and humidified flow. A sensor may determine a temperature of ambient air. The sensors 20a, 20b, 20c may be located remotely such as in the humidifier 12 and/or patient interface 14 as indicated in FIG. 1a. Alternatively as indicated in FIG. 1b the sensors 20a, 20b, 20c may be located within the flow generator 10 and/or humidifier 12. It should be appreciated that the number and location of sensors 20a, 20b, 20c may vary with the different respiratory apparatus arrangements and that the sensors 20a, 20b, 20c may be provided in the flow generator 10 and/or the humidifier 12 and/or the patient interface 14. It should also be appreciated that more sensors than those shown in FIGS. 1a to 1c may also be provided.

Figure 2A:
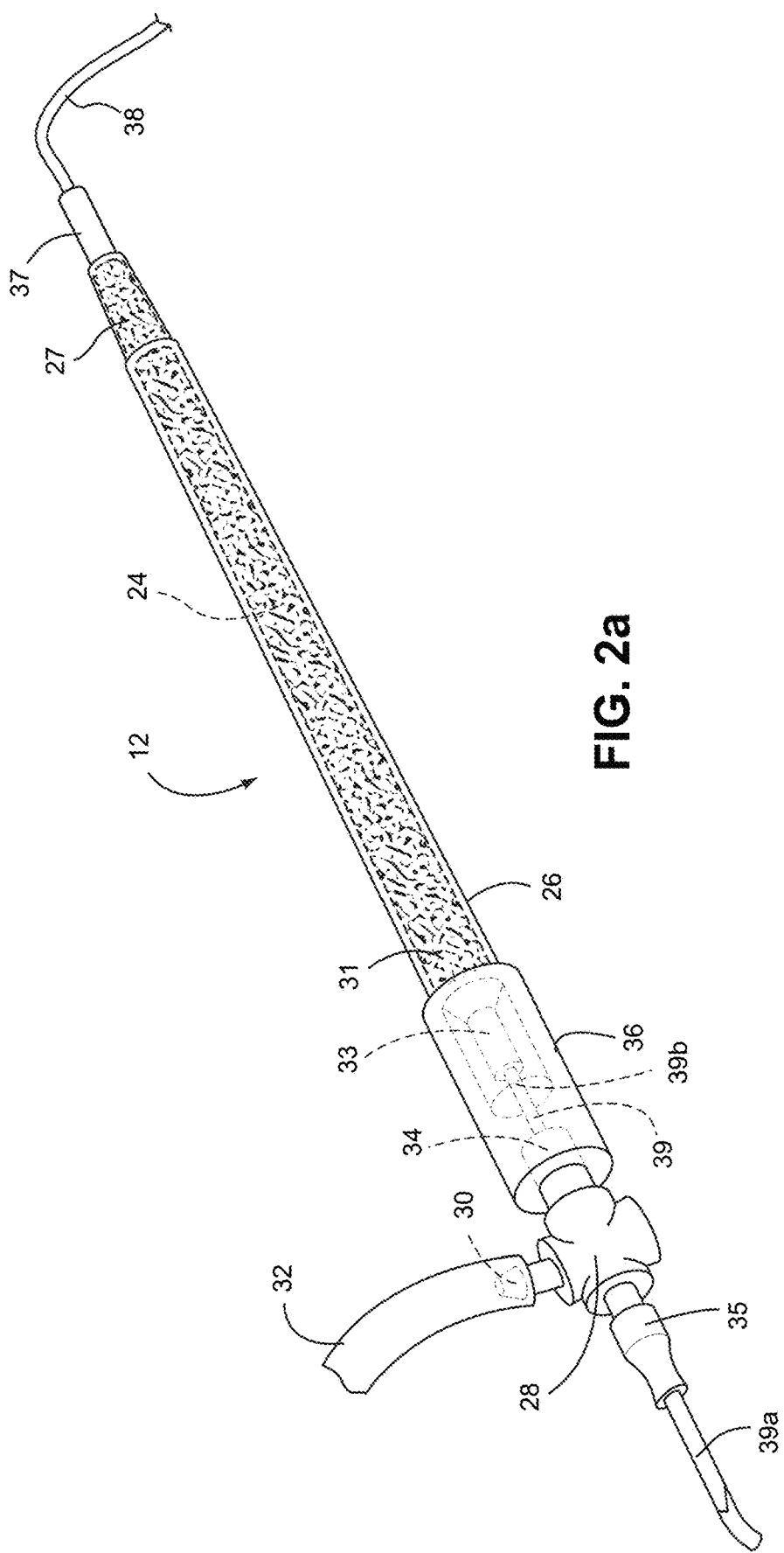
FIG. 2a is a schematic perspective view of an example of a humidifier assembly according to one aspect of the present technology.

The humidifier assembly 12 includes a generally porous structure 24 of a thermally conductive and electrically resistive porous material that is encased by an outer housing, for example a tube 26 which closely surrounds the porous structure 24. As illustrated the porous structure 24 may have a cylindrical shape; however other shapes may be utilised. One end 27 of the porous structure 24 may be a vapour outlet and may extend beyond the open end of outer tube 26, as shown in FIG. 2a.

A connector fitting 28 has a liquid (e.g. water) inlet 30, such as in the form of a spigot, to form a liquid inlet spigot, for connection to a liquid supply tube 32 leading from a liquid/water supply (not shown). Water may be provided to the water supply tube using a supply (not shown), such as a pump or by gravity feed or other known water transporting means, and a sealing tube connection spigot 34 for connection of a sealing tube 36 which forms a sealed connection between the connector fitting 28 and the outer tube 26. The connector fitting 28 may include a three-way or multi-way connector for example a Y or T shaped connector. An internal passageway within the connector allows water flow from the water inlet spigot 30 to spigot 34, then through the sealing tube 36 and through the porous structure 24.

The connector fitting 28 further includes a sealing connector 35 for connection of an electrically conducting wire 39 to the humidifier. The conducting wire 39 has a first end 39a that extends from an end of the humidifier to connect to a power supply and a second end 39b that is connected to the porous structure 24 within the outer tube 26. The sealing connector 35 is sealed to the conductor wire 39 passing co-axially with the sealing tube connection spigot 34, the second end 39b of the conductor wire 39 in turn being connected to an end 31 of the porous structure 24 located within the outer tube 26 by a connection with the first electrical connector 33, for example a crimp connection.

At the other, exposed, end 27 of the porous structure 24 is a connection with a second electrical connector 37, such as a crimp connector, for connection of a power lead 38. The power lead 38 with the conducting wire 39 applies a voltage across the porous structure 24 to operate as a resistance heater. The applied voltage may be low voltage DC, such as about 12V or 24V DC, e.g., taken from the flow generator power supply. Alternatively a separate power supply may be utilised. It should be appreciated that AC voltage may be used.

Figure 3A:
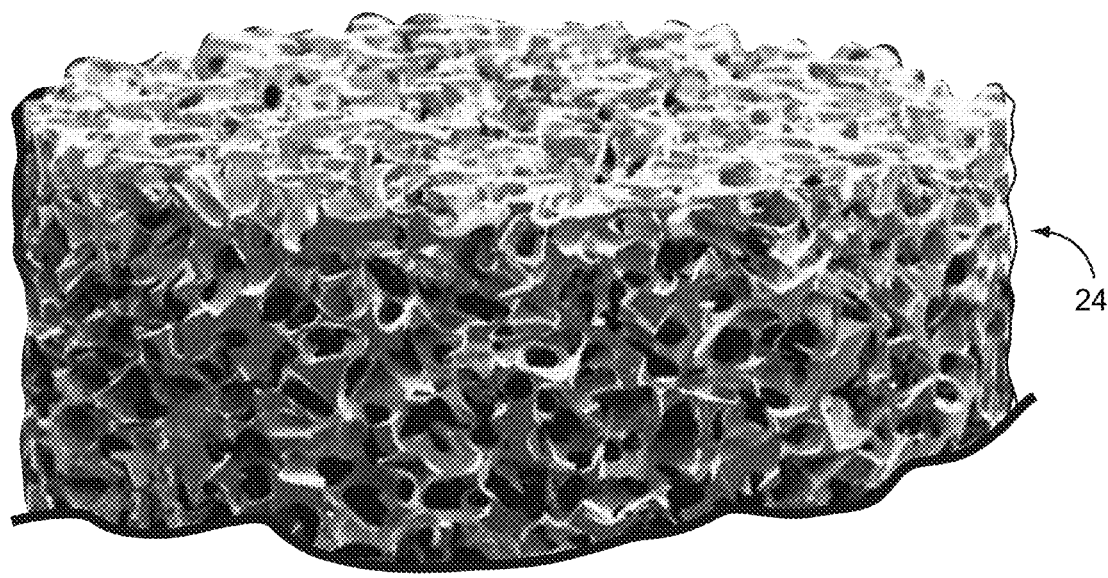
FIG. 3a is a photograph of an example metal foam material according to an aspect of the present technology.
Figure 3B:
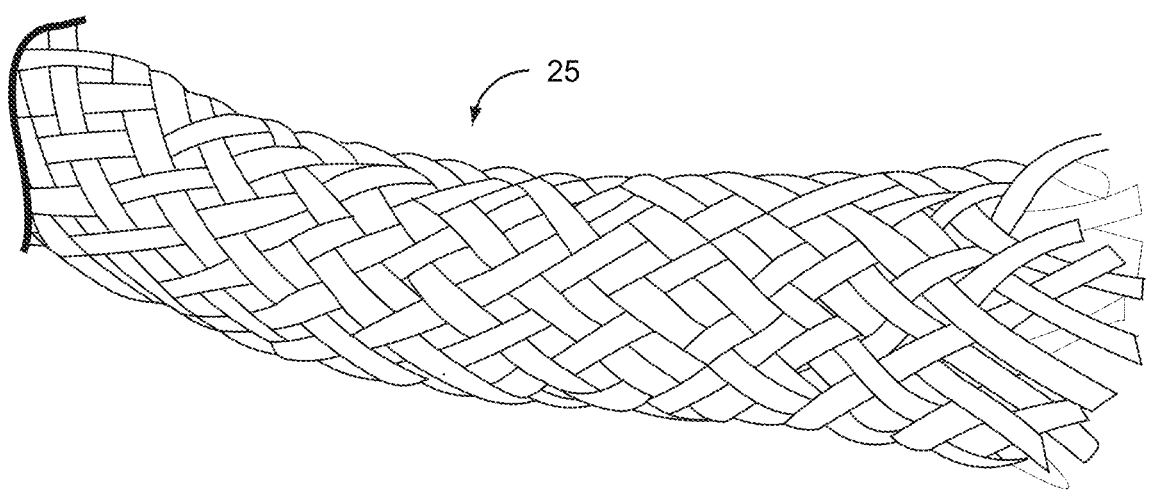
FIG. 3b is a schematic view of an example bundled fibre material according to an aspect of the present technology.

The porous structure 24 is composed of a thermally conductive, open pore material which allows passage of water and/or water vapour therethrough. The porous material has an open pore area which is sufficiently porous to allow water to flow through the material, such as pumped through or gravity feed through, from the inlet to the outlet without requiring excessive pressure. A detail view showing an example of the porous material of the porous structure 24 is illustrated in FIGS. 3a and 3b.

Example materials for the porous structure 24 may include porous metal or ceramic materials (e.g. silicon carbide or titanium nitride) having a thermally conductive and resistivity suitable for use as a resistance heater for the water contained within the pores of the material. Materials such as metal, resistive ceramic or carbon foams or fibres may be suitable.

Example materials for the porous structure are metal foams such as those available from Recemat International BV of the Netherlands. Nickel-chromium aluminium or Inconel® metal foams have been found to be suitable. Other example metals for the foam include super alloys such as chromium alloys. Example chromium alloys include MCrAlX, where M is one or more of Nickel (Ni), Cobalt (Co) or Iron (Fe) contributing at least about 50% by weight, Chromium (Cr) contributing between about 8% and 35% by weight, Aluminium (Al) contributing greater than 0% but less than about 8% by weight, and X contributing less than about 25% by weight, with X consisting of zero or more other elements, including but not limited to Molybdenum (Mo), Rhenium (Re), Ruthenium (Ru), Titanium (Ti), Tantalum (Ta), Vanadium (V), Tungsten (W), Niobium (Nb), Zirconium (Zr), Boron (B), Carbon (C), Silicon (Si), Yttrium (Y) and Hafnium (Hf). Another example chromium alloy is a nickel-chromium alloy or Inconel ® alloys. Other suitable materials may include porous ceramic materials such as silicon carbide, titanium nitride, or carbon such as pyrolytic carbon. Other porous metals of sufficient strength, corrosion and leaching resistance and appropriate electrical resistivity may also be used.

Example metal foams may be of the type formed by pyrolysis and/or metallisation of a polymer foam such as an open cell polyurethane foam. The metal foams may have an open pore volume of about 90% or greater, for example about 95%, and a pore size of about 0.1-2 mm, for example from about 0.2-1 mm, such as about 0.4 mm.

The porosity of the porous structure 24 may be substantially uniform, or may vary along the length and/or diameter of the cylinder.

Figure 2B:
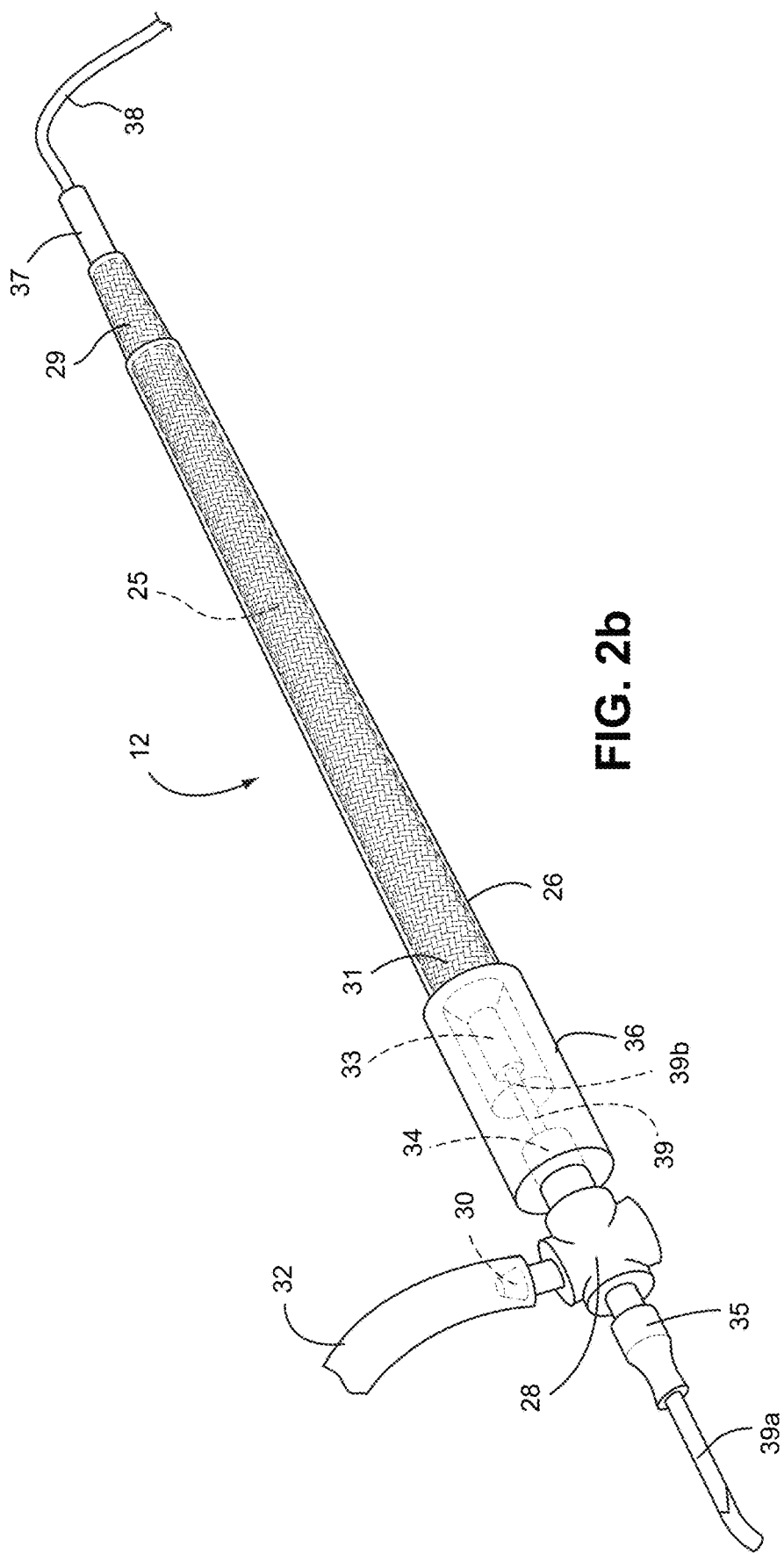
FIG. 2b is a schematic perspective view of another example of a humidifier assembly according to an aspect of the present technology.

FIG. 2b shows an alternative example wherein the thermally conductive and electrically resistive porous structure 25 comprises fibrous material, for example carbon fibres. Similar to the end 27 of the porous structure 24, an end 29 of the porous structure 25 may extend beyond an open end of the outer tube 26. The fibres may preferably be bundled in groups forming tow, twist, knit, braid, felt, woven fabric or tape structures. The fibrous structure having a plurality of apertures, or pores, which allow fluid to pass therethrough. A detail view showing an example of a braided bundle of fibres 25 is illustrated in FIG. 3b. Examples of fibrous materials include carbon fibres having a carbon content of greater than 50% and having precursors of Poly Acrylic Nitrite (PAN), rayon or pitch. The carbon fibre diameters may be less than about 20 microns, for example about 5 to 7 microns.

In the humidifier assemblies of FIGS. 2a and 2b, which are adapted for humidification of air for a respirator apparatus such as a positive airway pressure (PAP) device for treatment of sleep disordered breathing (SDB) of capacity approximately 100 L/minute flow capacity, a humidifier water throughput of approximately 0 to 10 ml/minute, for example 2 to 5 ml/minute, or 0 to 3 ml/minute has been found to be appropriate to achieve a relative humidity of about 80% relative humidity (RH) at 28° C. This requires a vaporisation power of up to about 240 W. Alternatively, with different geometries different power outputs may be used, for example power outputs of up to about 50 W, up to about 100 W or up to about 200 W.

A smaller water throughput capacity, such as about 0.5-2 ml/min, may be sufficient for many medical humidification applications.

Dimensions of the porous structure shown in FIG. 2a may range from about 1 mm-5 mm diameter, for example about 2 mm, and a length of about 20 mm-200 mm, for example about 100 mm. This provides a volume range for the porous structure of approximately 10 mm$^3$ to 4000 mm$^3$, for example 15 mm$^3$ to 500 mm$^3$, such as 314 mm$^3$.

The outer tube 26 surrounding the porous structure 24, 25 closely surrounds the porous structure 24, 25 so as to contain the water to travel through the porous structure and to ameliorate by-passing of the porous structure. The outer tube 26 may be formed of materials which are electrically and thermally insulating, are thermally shock resistant, and which have a low specific heat capacity. A ceramic tube such as alumina or fused quartz may be used, or alternatively a polymer such as heat shrink or silicone rubber tubing may be applied to the outer surface of the porous structure 24, 25. In other forms, it may not be necessary to use an outer tube 26, for example the porous structure may be located in within some other container.

In operation, a controlled flow of water may be provided by a supply means (not shown), for example a micro-pump such as a piezo-electric pump, under pressure from a water supply (also not shown) to the water inlet 30 of the connector fitting 28. The supply means may be configured to deliver a desired volume of water to the water inlet 30. This flow of water passes into and through the pore structure of the porous structure 24, 25 of the humidifier whilst electrical current is also passed through the electrically resistive material of the porous structure 24, 25. The material of the porous structure 24, 25 thus acts as a resistance heater for the water, which is in intimate contact with its pore structure, heating and vaporising the water as it flows from the water inlet to the vapour outlet 27 of the humidifier. Steam is thus formed, and is expelled from the vapour outlet 27 of the porous structure 24, 25 and delivered to the respiratory gas flow path. The vapour outlet 27 may extend past the end of the surrounding outer tube 26 and into the air delivery tube to deliver the steam into the respiratory gas flow path being provided to the patient.

In one unillustrated example, the porous structure 24, 25 may be tapered so as to increase in diameter from the water inlet to vapour outlet, e.g. frustro-conical, to compensate for the expansion of the steam as the water is vaporised. In this case, the outer tube 26 will be correspondingly shaped to conform to the shape of the porous structure 24, 25.

With comparatively low pressure required to propel the water through the porous structure 24, 25 due to the high open area, and controlling the level of humidification by controlling the current passing through the porous structure 24, 25, a gravity feed water supply means such as an external water bottle or a collapsible bladder may be utilised in place of the pump. Distilled water may used to prevent clogging of the porous structure 24, 25.

The humidifier arrangement may thus provide a relatively compact, efficient and readily controllable humidification apparatus having low thermal mass and thus rapid control response compared with the prior art water tub humidification arrangements. More rapid and accurate control of the humidification may be achieved, as thermal lags are reduced.

FIG. 7 illustrates an alternative example of the present technology. As shown, the humidifier (or humidifier assembly) 50 includes a generally porous structure 52 of a thermally conductive and electrically resistive porous material. The arrangement of the humidifier 50 is generally similar to the example shown in FIGS. 2a and 2b, except in this example, the porous structure is encased in an outer housing having two parts 54a and 54b (or alternatively, two separate housings 54a, 54b). A portion of the porous structure 52 is exposed at an open end of the housing 54a, 54b, being a steam outlet 56 of the humidifier 50. On the other end, a connector fitting 58 receives a liquid (e.g., water) from a liquid supply tube 60, and provides the liquid to the sealing tubes 62 via the sealing tube connection spigots 64. Liquid may be provided using a pump or by gravity feed or other known liquid transport means.

Air Heater Coil

Figure 4:
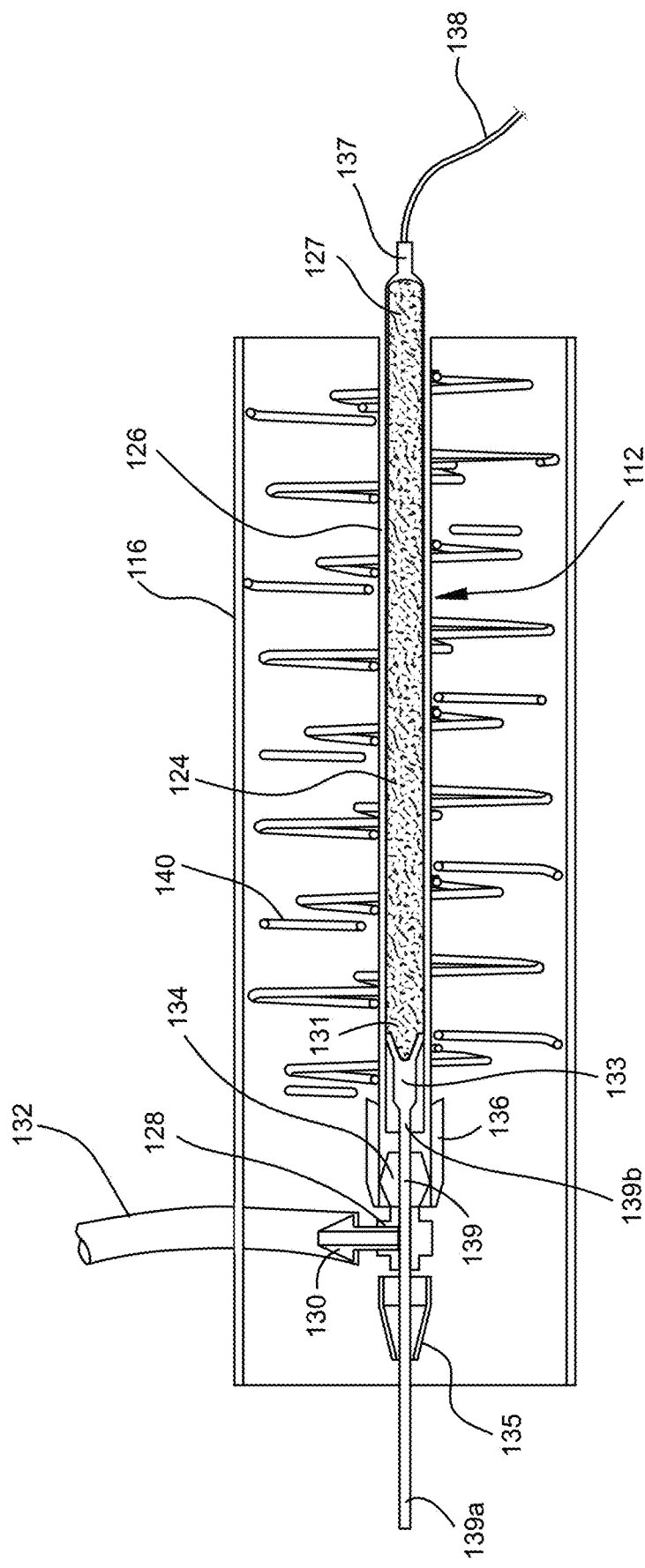
FIG. 4 is a longitudinal cross section showing the mounting of the humidifier within the air delivery tube of a respiratory apparatus according to an aspect of the present technology.

FIG. 4 illustrates an example in which the humidifier 112, generally similar to the humidifier shown in FIGS. 2a and 2b described above, is supported within an air delivery tube (or air delivery conduit) 116 of a respiratory apparatus such as a PAP device, or may be supported within a portion of the air delivery tube 116. Reference numbers beginning with a "1" designate similar features as those in FIGS. 2a and 2b (e.g. reference number 128 designates a connector fitting).

When heating air in an air path, it may be desirable to have an air heater having a small volume. This could provide a smaller CPAP device, lower costs and reduce power consumption (e.g., longer battery life for portable devices). An air heater may be used with or without a humidifier within a respiratory system.

For a given air conduit, its cross section would likely be uniform along the longitudinal length (e.g. generally round), so its length would determine the volume. To heat air efficiently, the flow of each airstream should come in contact with (or be very close to) the heating wire for effective heat transfer. If the flow is laminar, it may be desirable for the total cross section of the air path to be "covered" with an axial projection of the heater wires and to have no (or minimal) overlapping wire projections.

A porcupine heater coil may be made on a mandrel by wrapping the wire under tension around said mandrel. If the mandrel has a circular cross section, the resulting form would be a helical spring as shown in FIG. 8.

If the mandrel has a high aspect ratio rectangular cross section, then the resulting form would be a series of star shaped wire bends as shown in FIG. 9. A porcupine coil is wound around a mandrel and when finished is allowed to spring off the mandrel to take the shape of the coil with staggered "star" shaped elements having points or corners on the outer periphery. However, this may result in a large open space along the centre of the coil where no air heating will occur. The length of heating wire in the porcupine coil is concentrated around the central hole area and only the corners or points are on the outer diameter (when looking at the end view).

Each of these shapes has a core in the centre which does not heat the air stream flowing through the centre core. To evenly heat the air stream, it would require heat diffusion from the outer hot air to the cooler central air stream. Alternatively, turbulence may be induced to mix the airstream to obtain a uniform air temperature. However, inducing turbulence may increase the impedance of the air flow and increase the power required for the system.

Another issue with a porcupine coil is that the projected wires may be concentrated in a fairly narrow annular band (depending on wire tension and mandrel shape when winding), and the air streams flowing through this narrow annular band would generally receive most of the heating. This may cause uneven air heating and may result in further inefficiency.

A wire bender may be used to bend the wire into a structure that achieves a heating area covering an entire or substantially all or most of the cross section of an air tube, so that air heating may be completed in a shorter length. A coil may be formed so that the loops of wire (that go around the centre open core area, as in a porcupine mandrel formed coil) are instead bent as they approach the centre core. A combination of a number of coil loops may thus form the periphery of the centre core. This allows the centre core dimensions to be variable, or may be formed such that the centre core closes up completely, that is, effectively filling the complete or substantially all or most of the cross section with the heating wire.

By choosing the angle of each wire loop around each 360° turn to not be a factor of 360, the subsequent coils would not align with the first "row". This would allow coverage of a different portion of the cross sectional area by presenting more heating wire to the air steam. The radius of curvature of the outer bend portion and the inner bend portion may be used to determine the size of the centre core open cavity. For example, determine the shape of the coil by the outer radius, the outer length of the outer radius, the inner radius and the inner length of the inner radius, as well as the pitch of the coil. These dimensions may also determine the inner centre open core space diameter and the outer diameter of the whole coil structure.

Figure 6A:
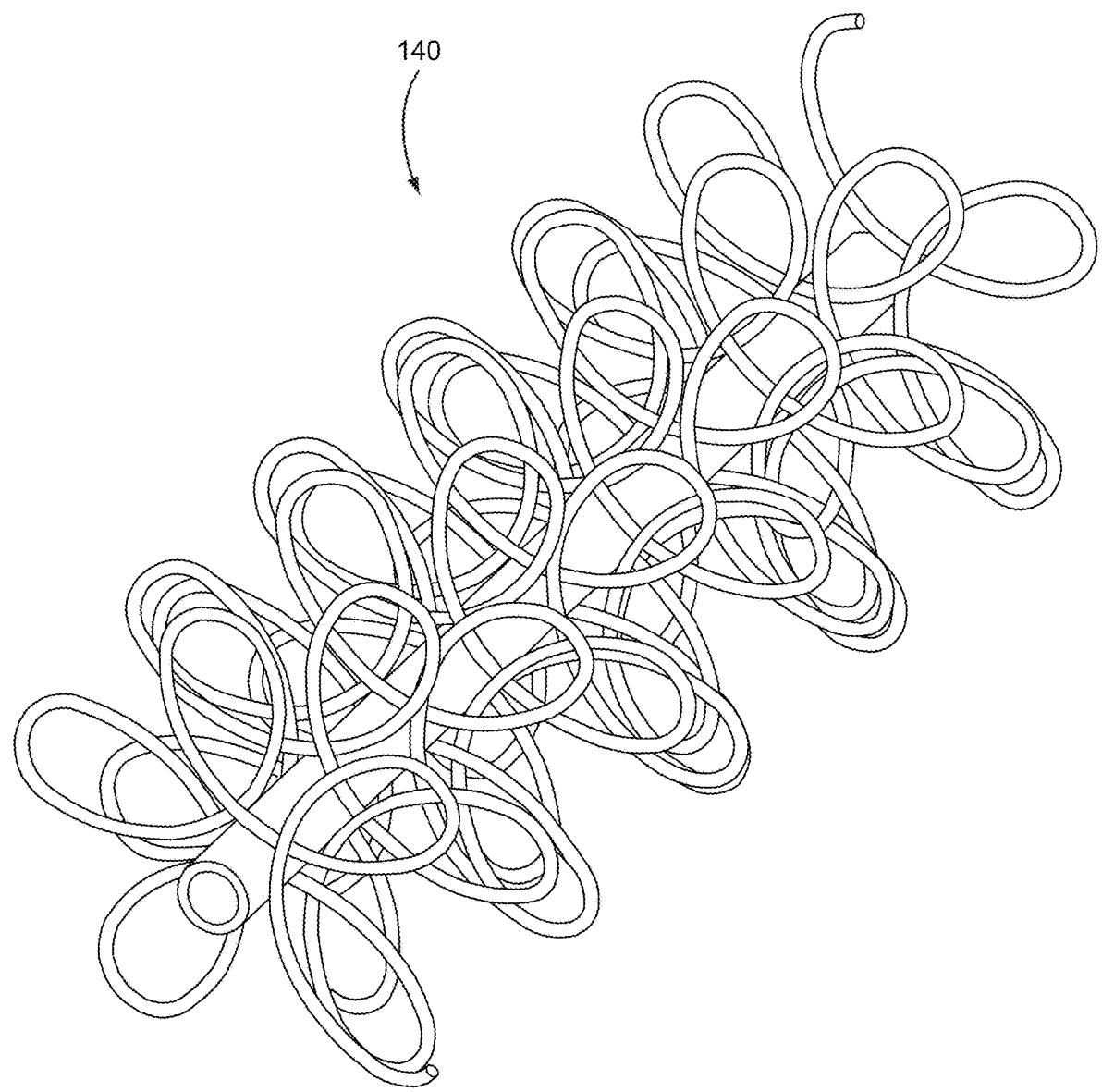
FIG. 6a is an isometric view of the mounting structure of FIGS. 4 and 5.
Figure 6B:
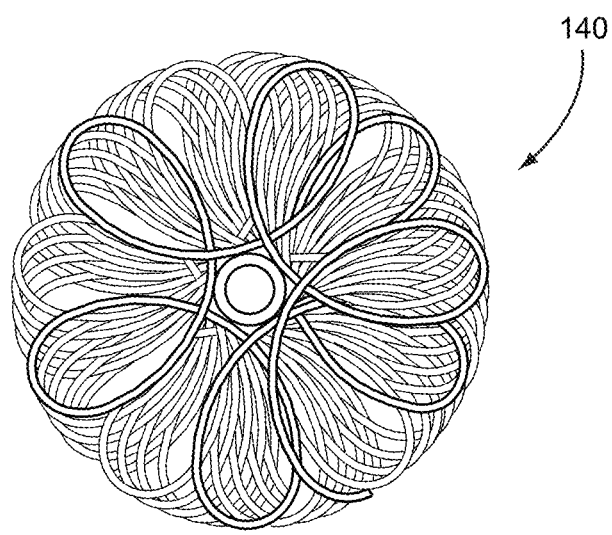
Figure 6C:
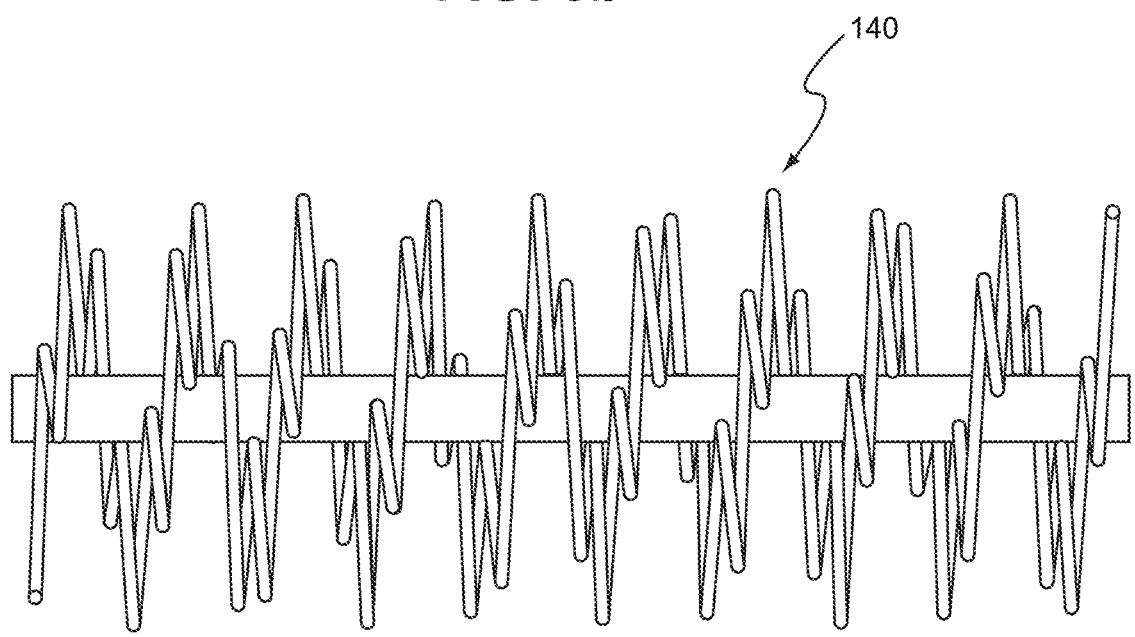
Figure 6D:
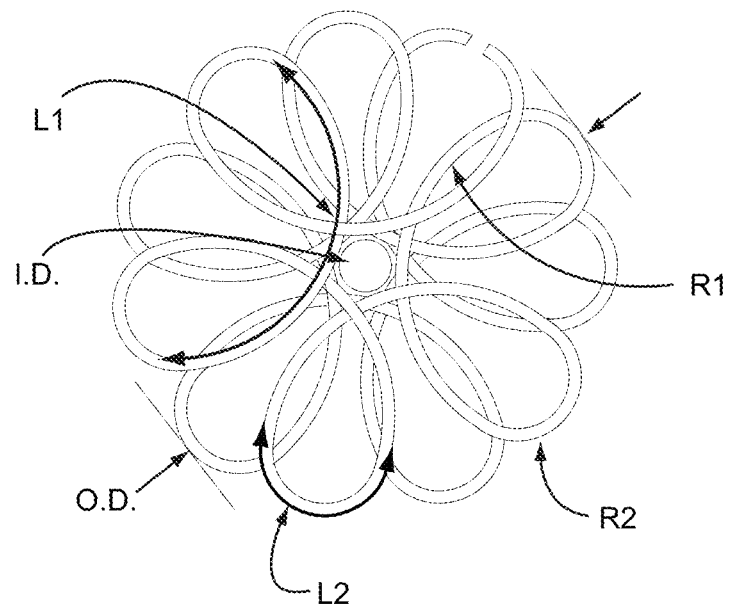
FIG. 6d is an illustration of dimensions of the coils of the mounting structure of FIGS. 6a-6c.
Figure 6E:
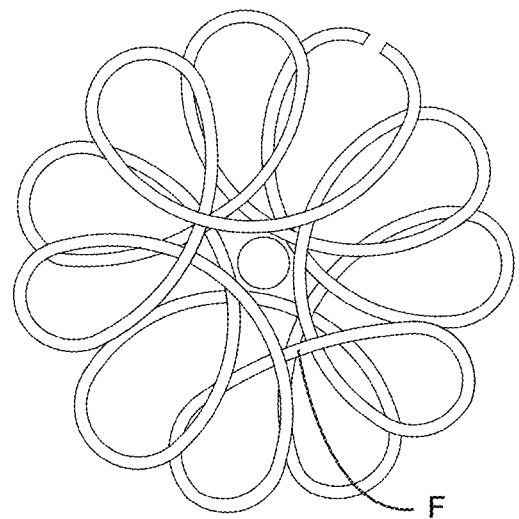
FIG. 6e is a side view of a mounting structure according to another example of the present technology.

An example of the dimensions of the coil is shown in FIG. 6d. The coil may have an outer diameter O.D. of about 20 mm to 30 mm, for example about 25.4 mm. The coil may have an inner diameter I.D. of about 1 mm to 5 mm, for example about 3.0 mm. The loops of the coil may have an first length of about 15 mm to 25 mm, for example about 19.3 mm, and a second length of about 5 mm to 12 mm, for example about 8.85 mm. The first length L1 may be formed by bending the wire at a radius R1 of about 15 mm to 20 mm, for example about 17.4 mm, and the second length L2 may be formed by bending the wire at a radius R2 of about 1 mm to 5 mm, for example about 3 mm.

The heat radiated by the coil structure may be determined by the resistivity of the coil structure, the longitudinal length of the coil structure and the cross sectional diameter of the coil structure.

The humidifier 112, schematically represented in FIG. 4, is supported within the air delivery tube 116 by means of one or more mounting structures 140 such that the major axis of the humidifier is generally parallel to the axis of the air delivery tube 116 so as to present minimal interference to the air flow within the tube. That is, the humidifier is mounted substantially parallel to the longitudinal axis of the air delivery tube. Alternatively, the humidifier may be mounted in a different configuration that is not along the longitudinal axis, but wherein the steam outlet is exposed to the air flow.

Figure 5:
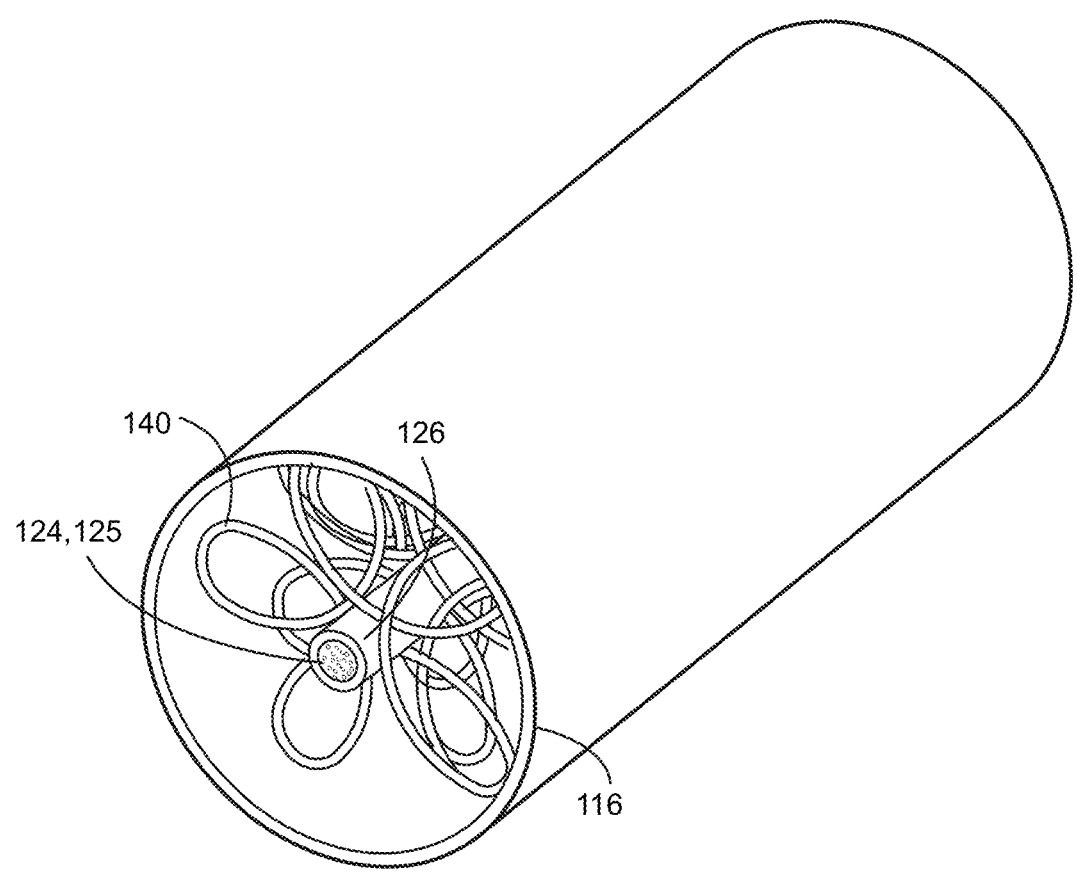
FIG. 5 is an isometric view of the mounting structure of FIG. 4.

The mounting structure(s) may comprise a coil structure such as a 'helical coil' or a 'porcupine coil' arrangement, for example as illustrated in FIGS. 8 and 9, or a 'rosette coil' arrangement formed of wire to create a formation which engages with the inner surface of the air delivery conduit 116 and with the outer surface of the humidifier 112, to hold the humidifier substantially co-axially within the tube, as illustrated in FIGS. 5 and 6. The "rosette coil" structure may be formed using a wire bending machine. In this arrangement the mounting structure may also optionally be used as a resistance heater for heating the air flowing within the air delivery tube 116 prior to receiving the water vapour from the humidifier, so that take-up of the vapour by the gas flow is increased.

Referring to FIGS. 4-6e, a mounting structure 140 in the form of a "rosette" heating coil is shown. In the rosette heating coil the wires are not wrapped around a mandrel but are formed on a wire bending tool using two distinct radii. The form of the rosette coil allows a proportionally larger length of heating wire to be located at the periphery of the coil to heat the larger volume of air that flows in this region. This form also allows a relatively small hole down the centre of the coil (and may be adjusted in size) and may be used to support the outer tube 26 that encloses the steaming element.

The "petals" or loops of the rosette are designed so that there are a multiple of them on each section or "flower" and the next flower has the petals offset or overlapping to the previous one so the air path along the tube is ensured of being in close proximity to any part of the heating wires at some stage of its flow. The appropriate offset may be chosen so that there is complete coverage of the cross section of the annular area between the outer tube 126 and the air delivery conduit 116. The design produces a more compact air heating coil than prior art heating coils.

Humidification and Water Management

The controller 18 (as shown in FIG. 1) may receive signal/s from the at least one sensor 20a, 20b, 20c and be configured to control the humidifier to provide the humidified flow of breathable gas at a predetermined temperature and a predetermined relative humidity. Further, the controller 18 may be configured to control the supply of power such that vapour is delivered during a portion of a phase of a patient's breathing cycle, for example only during the patient's inspiratory phase. By doing this, water usage may be managed as required, and water conserved to reduce wastage.

The operation of the humidifier may be arranged such that, from known ambient conditions, a desired condition at the patient interface end may be obtained. For example, first measure the ambient temperature and relative humidity (or measure temperature and relative humidity at any identical point prior to the humidifier, for example within the flow generator). Using these measurements, calculate the absolute humidity by the below formula.

$$P_{ws} = A \cdot 10^{\left(\frac{m \times T}{T+T_n}\right)} \text{ (hPa), where} \quad (6)$$

$A, m, T_n$ = constants see table 1

$T$ = temperature (° C.)

TABLE 1

| Temperature range (° C.) over water: | A | m | Tn | max error |
|---|---|---|---|---|
| −20 . . . 50 | 6.1162 | 7.5892 | 240.71 | 0.09% |
| 50 . . . 100 | 5.9987 | 7.3313 | 229.1 | 0.01% |

| Item | Definition |
|---|---|
| % RH | % Relative humidity |
| A, AH | Absolute humidity |
| $P_{ws}$ | Saturated partial pressure of water vapour over water |
| T | Temperature |
| $P_w$ | Partial pressure of water vapour over water |
| F | Air flow rate in litres per minute |
| Q | Water volume in millilitres |
| hPa | hectapascal |
| K | Kelvin degrees |
| C | Celsius degrees |
| Td | Dew point temperature (not used in these calculations) |

Then calculate the water vapour pressure from % RH:

Calculate $P_w = P_{ws} * RH/100$ (in hPa!)

EXAMPLE

The ambient temperature is 40° C. and the RH is 50. Calculate $T_d$:

$$P_w = P_{ws}(40°\,C.) * 50/100 = 36.88\text{ hPa}$$

Example for 30° C. and 80% RH, (Target Point)

$$Pws = 6.1162 \times 10^{*(7.5892 \times 30/(30+240.71))}$$

$$Pws = 42.415\text{ hPa}$$

and $$Pw = Pws \times RH/100$$

$$Pw = 33.932\text{ hPa}$$

Absolute humidity is defined as the mass of water vapour in a certain volume. If ideal gas behaviour is assumed the absolute humidity can be calculated using (17):

$$A = C * P_w/T (g/m^3), \text{ where} \qquad (17)$$

C=constant 2.16679 gK/J
$P_w$=vapour pressure in Pa
T=temperature i K

Example

The ambient temperature is 20° C. and the relative humidity is 80%. Calculate absolute humidity:

$$Pw = P_{ws}(20°\,C.) * 80/100 = 18.7\text{ hPa}$$

$$A = 2.16679 * 1.870/(273.16+20) = 13.82\text{ g/m}^3$$

Example for 30° C. and 80% RH, (Target Point)

$$Pw = 33.932\text{ hPa(from above)}$$

And $$AH = 2.16679 \times 3393.2/(273.16+30)$$

$$AH = 24.252\text{ g/m3(or mg/L)}$$

Therefore the Target AH is 24.252 mg/L
For a given flow rate F (in L/min), the quantity of water (Q) to be injected into the airstream is:

$$Q = (24.252 - AH\text{ at ambient}) \times F\text{ mg/min}$$

For water near room temperature, 1 mg~1 mL.

Figure 12:
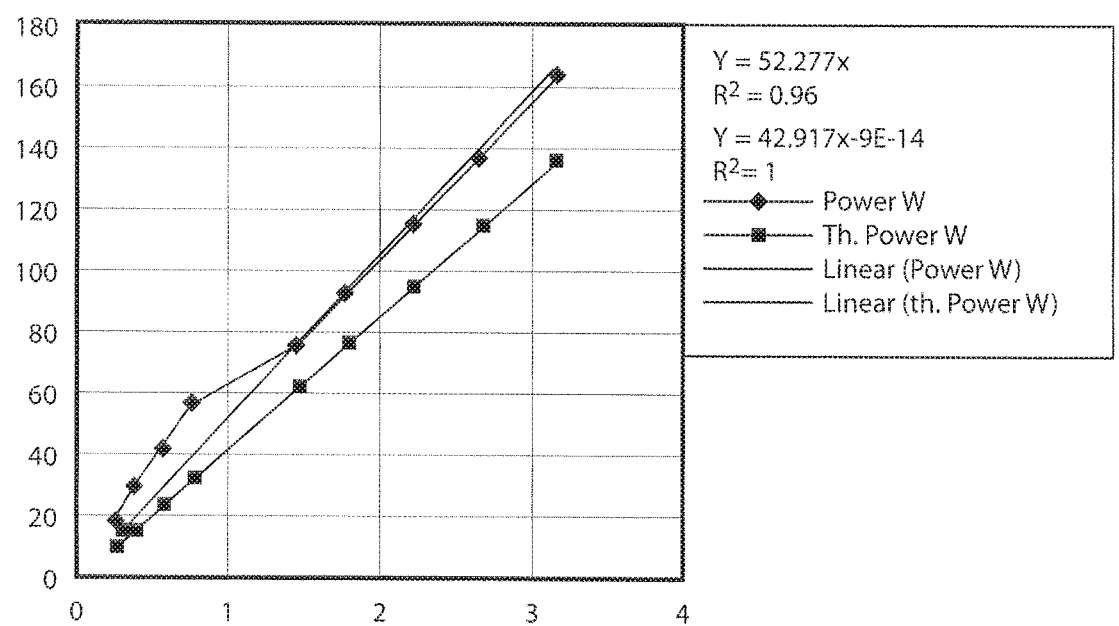
FIG. 12 is a chart showing empirical values of power required to vaporise an input water flow.

From the water flow rate, the power required may be determined by reference to a chart (FIG. 12) derived empirically.

Figure 10:
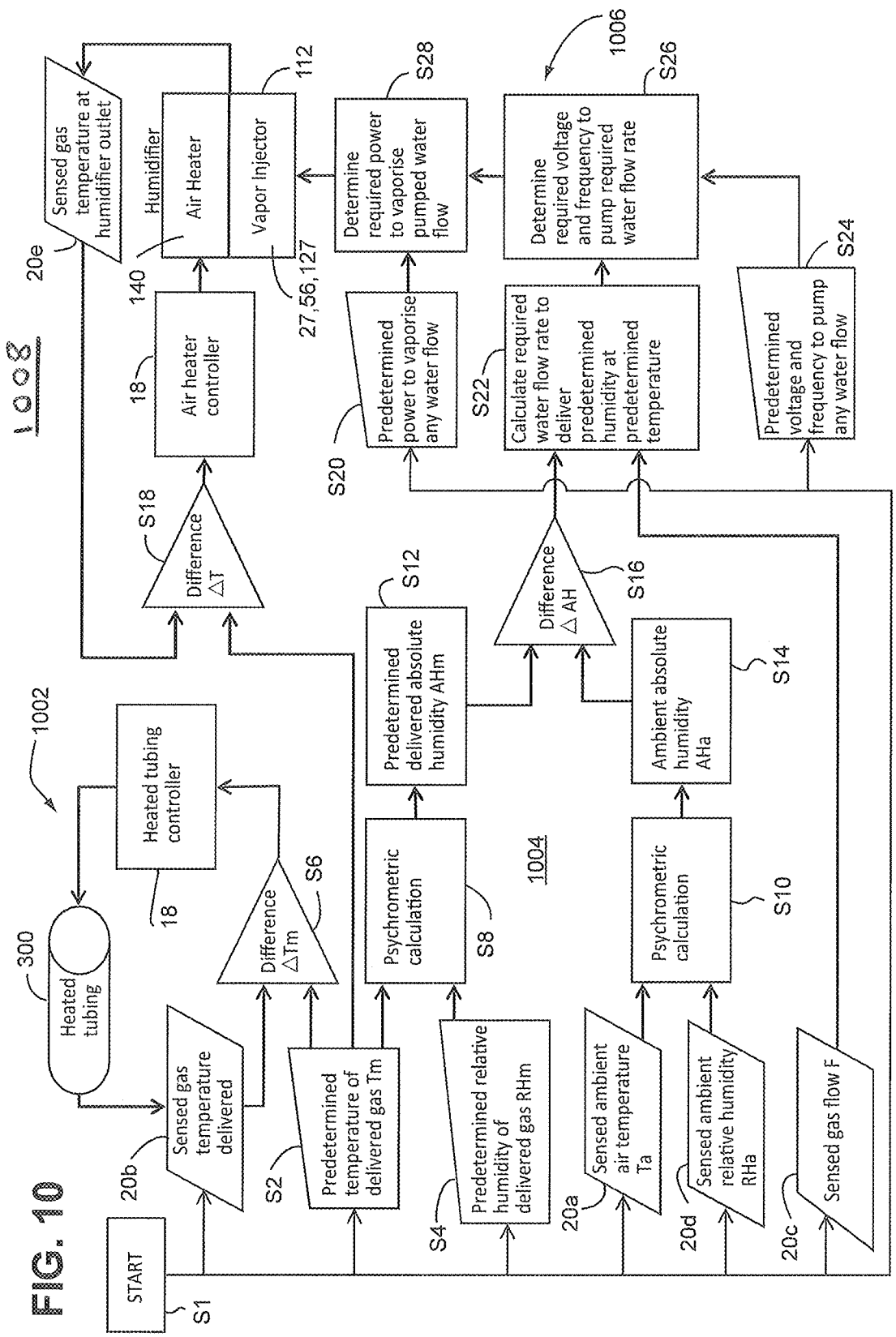
FIG. 10 is a flow chart of a mode of operation of a humidifier according to an example of the present technology.

Modes of Operation
Humidifier Controls
FIG. 10 shows a flow chart of an example mode of humidifier operation. Process steps 1002 show the control of a heated tubing 300. The heated tubing may be similar to that described in, for example, U.S. 2008/0105257 A1 and/or U.S. 2011/0023874 A1, the entire contents of both being incorporated herein by reference. The process begins at SI and includes receiving measurements of sensed gas temperature delivered to the patient interface. The sensed gas temperature may be provided from a sensor 20b. A predetermined temperature Tm of gas to be delivered to the patient interface is provided at S2. The predetermined temperature Tm may be, for example, selected by a user (e.g. clinician) or patient from an input of an apparatus as shown in, for example, FIGS. 1a to 1c. The predetermined temperature may also be provided as disclosed in, for example, U.S. 2009/0223514 A1 and/or U.S. 2011/0023874 A1. The sensor 20b measures a sensed gas temperature and compares with a desired (i.e. predetermined) target temperature provided at S2. The difference ATm is determined at S6 and is fed back to the controller 18 to control the operation of the heated tubing 300. This process may be similar to that disclosed in U.S. 2009/0223514 A1, the entire contents of which are incorporated herein by reference.

Process steps 1004 determines the required water flow rate to deliver a desired or predetermined target humidity at a desired target temperature. As previously described in the example calculations, the ambient absolute humidity may be calculated by measuring the ambient air temperature and ambient relative humidity. This ambient absolute humidity is compared with the target required absolute humidity (calculated using the target (e.g. desired or predetermined) temperature and relative humidity) to calculate the quantity of water required. For a sensed gas flow, and knowing the quantity of water that need to be delivered per unit volume of gas, the water flow rate may be calculated. As shown in FIG. 10, the predetermined delivered gas temperature Tm is provided at S2 and a predetermined relative humidity RHm to be delivered to the patient interface is provided at S4. The predetermined relative humidity RHm may be, for example, selected by the user or patient in a manner similar to that described in, for example, U.S. 2009/0223514 A1 and/or U.S. 2011/0023874 A1. The predetermined values of RHm and Tm are provided to a psychrometric calculation at S8 and the predetermined absolute humidity AHm to be delivered to the patient interface is provided at S12.

Process steps 1006 show the controls of the power input to both pump the water and heat the heating element. Using the calculated water flow rate, and knowing a predetermined energy required to adequately pump, heat and vaporise the water, we can determine the voltage, frequency, power etc required for controlling the process of the steam injector. The sensed gas flow F, determined for example by a sensor 20c, and the difference ΔAH are used at S22 to calculate the required water flow rate to deliver the predetermined humidity at the predetermined temperature. Alternatively the flow rate may be estimated based on the motor current as described in US 2010/0319697. The predetermined voltage and frequency to pump any predetermined water flow rate is determined or provided at S24 and at S26 the required voltage and frequency to pump the required water flow rate is determined. The predetermined power to vaporise any liquid flow at S20 is used along with the required pump voltage and frequency to determine at S28 the required power to vaporise the pumped liquid flow. The required power determined at S28 is provided to the humidifier, e.g. to the controller 18.

Process steps 1008 show the controls of the air heater coils of the mounting structure 140. By sensing the temperature at the humidifier outlet, with for example a sensor 20e, and comparing with the desired target air flow temperature Tm, the difference ΔT between the sensed temperature provided by the sensor 20e and the predetermined temperature Tm can be determined at S18. The difference ΔT can be provided to the controller 18 to provide feedback control of the air heater of the mounting structure 140.

It should be appreciated that the controller 18 may be provided to control the liquid transport (e.g. the pump), the air heater (e.g. the coil of the mounting structure 140), the heated tubing 300, the humidifier (e.g. the humidifier 112). It should also be appreciated that the controller 18 may be a plurality of controllers and that the plurality of controllers may be provided in the various components. For example, a controller may be provided in the flow generator, the humidifier, the pump, the heated tubing, etc. It should also be appreciated that the controller, or each controller, may be in the form of, for example, a microcontroller or a specially programmed general purpose computer, or an ASIC. It should further be appreciated that the process shown in FIG. 10 may be executed from a software program or other executable code or instructions stored in a memory provided in the controller. It should be even further appreciated that the memory(ies) of the controllers) may include, for example, empirically determined coefficients and/or look up tables for use in various psychometric and other calculations of the process.

Figure 11:
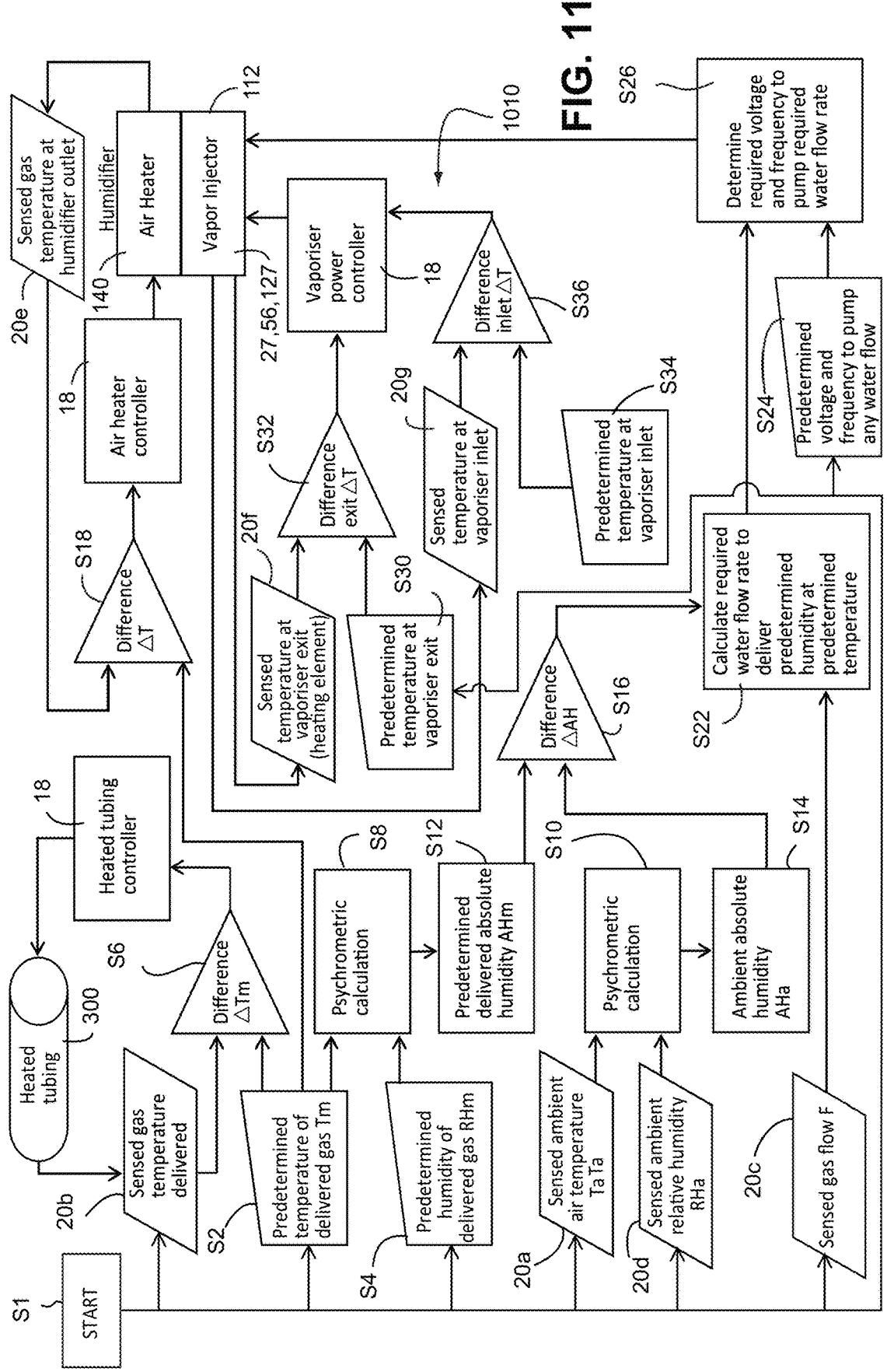
FIG. 11 is a flow chart of a mode of operation of a humidifier according to another example of the present technology.

FIG. 11 shows a flow chart of another example mode of humidifier operation. FIG. 11 includes all the process steps shown in FIG. 10 and further includes control steps 1010 for controlling the operation of the heating element. As shown in 1010, the operation of the heating element may be controlled by predetermining a desired target heating element outlet temperature at S30. For example, this predetermined temperature may be a minimum temperature that is required to fully vaporise the liquid flowing through the heating element. By monitoring the sensed temperature at the heating element outlet with, for example a sensor 20f, the heating element can be controlled to ensure the minimum temperature is maintained by determining a difference ΔT at S32 and using a feedback control loop. It should be noted that in some forms of the present technology, not all the steps shown in FIG. 10 or 11 may be required. In some cases, alternative steps may be included, and other steps may be omitted.

Balanced Circuit Test

A balanced circuit test may be used to detect if there is a fault with the air heater and/or the heating element. The balanced circuit test may be enabled by providing a connection to the center of the heating element, in addition to the two electrical connection points provided at each end of the heating element. Measuring a voltage, current or resistance etc from the center tap to each of the end electrical connection points, the result of each segment should be the same (balanced) as the other. If the measurements do not match, it may indicate a fault of the circuit.

Temperature Plausibility Mode

By comparing the sensed temperature at different sensors when the heating element and/or air heater is not turned on, the system may be enabled to detect faults in a sensor that does not provide the same result as the other sensors under conditions, when they should provide the same result.

Configuration of Water Supply and Heaters

The liquid supply may be a water bottle that is connected to the pump inlet such that water may be supplied to the pump and be pumped to the inlet of the heating element. The bottle may be rigid or collapsible. At the outlet of the heating element, the water becomes converted to steam and the generated steam is injected into a pressurised air stream. To improve the pump operation, the water supply may be pressurised. This may balance the system, so the pump does not operate against the pressure experienced at the heating element outlet. An example configuration is fitting a rigid liquid container with an opening to the top of the bottle which is connected to the pressurised air stream. Alternatively, a collapsible container may be provided within a rigid housing which is pressurised. The container may also be allowed to slightly inflate/deflate with a varying pressure. Such a configuration may allow the use of a zero-head pump for water.

In another alternative, a patient's expiration may be directed to actuate a pumping of the water into the heating element. For example, using a pressure dampening mechanism and controls, the expiratory pressure force from a patient may be applied to pump the water supply when the patient's inhalation cycle is occurring. This may assist the pump or replace the functions performed by the pump.

A number of humidifier system configurations may be provided to implement the present technology. For example, the water supply may be located near or within the flow generator/humidifier system; or external to the system and connected to the humidifier via a conduit. The pump may be provided near or within the flow generator/humidifier system; or external to the system as described above with the water supply; or provided near the patient interface (mask) and connected to the water supply and heating elements via conduits. The air heater may be provided near or within the flow generator/humidifier system; near or within the airflow tubing, at a location near the flow generator/humidifier system; at a location along the length of the airflow tubing; or near the patient interface. The heating element may be provided near or within the flow generator/humidifier system; near or within the airflow tubing, at a location near the flow generator/humidifier system; at a location along the length of the airflow tubing; or near the patient interface. It is preferable to locate the heating element downstream of the air heater, so that the air heater heating the air flow may help maintain the water holding capacity of the air flow and maintain the relative humidity.

Sensors

Temperature sensors may be added to the inlet end and outlet end of the humidifier to detect fault conditions, for example for use in preventing the heater element from overheating (e.g. from lack of water). The conditions detected by the sensors may be indicative of fault conditions.

For example, if the outlet sensor detects a temperature of less than 100 C, it may be an indication that steam is not being formed and water may be coming out instead of steam. This condition may be the result of a heating element failure, incorrect water flow rate, and/or incorrect power level. If the outlet sensor detects a temperature that is significantly greater than 100 C, it may be an indication that water may have stopped flowing. This may be the result of a pump failure and/or blockage.

If the inlet sensor detects a temperature that is near room temperature and power is applied, it may be an indication that water is flowing (i.e. the heating element is not dry heating). If the inlet sensor detects a temperature that is significantly greater than room temperature, it may be an indication that water is not flowing, or too much power is being applied.

The sensors generally have an expected operating range during normal operation, so any deviation from the expected operating condition may indicate sensor failure. The sensors may also be used to control the power to the heating element instead of using an empirical chart such as Chart 1.

An air temperature sensor may be located downstream of the air heater and steam injection outlet location. This sensor may detect the real time air temperature and be in close loop feedback to control the power applied to the air heater coil structure. Accordingly, the humidified air temperature may be controlled and adjusted to the desired condition, for example 30 C.

Sterilisation & Cleaning Modes

The humidifier may utilise dry heat sterilisation to destroy micro-organisms. That is, heating the humidifier in the absence of water vapour for a period of time, such that micro-organisms are destroyed by the heating process. Dry heat sterilisation for a CPAP humidifier may be activated for example during day time, when the patient is not using the device. Alternatively, it may run before and/or after a patient's therapy session.

Some example heating temperature-time processes that may be effective for dry heat sterilisation are:

160-170 degrees C. for 120 minutes;
170-180 degrees C. for 60 minutes; and
180-190 degrees C. for 30 minutes.

Heating at a higher temperature for a shorter period of time, or lower temperature for a longer period of time, may also be effective.

As previously described, the humidifier may have temperature sensors located at the inlet and outlet ends of the heating element. The temperature levels detected by the sensors may be input into a close loop feedback system, to control the heating element to heat to desired temperature levels for a chosen time period. Alternatively, or in combination with the heating element, the air heater coil may also be heated for the dry heat sterilisation process.

The humidifier may have wet heating/unheated cleaning functional modes for removing residues, deposits and/or micro-organisms from the heating element. The humidifier may be configured to allow a liquid flow through the heating element (with or without activation of heating element resistance heating) to flush out any unwanted particles or organisms. The cleaning mode may be initiated for example before and/or after a patient's therapy session. The cleaning mode may be set up by varying control parameters of liquid flow rate, heating temperature, and run continuously or in varying frequency periods. The timing of the activation/deactivation of the cleaning mode may be monitored and/or controlled using a timer.

One advantage of certain aspects of the present technology is that a smaller and/or more compact humidifier may be provided. For example, the volume of water may be reduced. Another aspect of certain forms of the present technology is that the forms may be cheaper, for example where the water is in a separate system and not pressurised, then certain pressure seals may not be required within the tub. In certain forms, there may be less of a need for spillback protection since less water is present.

An advantage of certain aspects of the present technology is that a humidifier may be provided that can respond more rapidly to changing circumstances, for example on a breath by breath basis, or to lead to a more rapid start up. An advantage of certain aspects of the present technology is to provide more precise control over the amount of humidification provided.

Another advantage of certain aspects of the present technology is a more efficient energy use, through the use of a more efficient heating element. Another advantage of certain aspects of the present technology is that they enable a wide range of different shapes and/or configurations to be manufactured, for example, a heating element that may be arranged in a variety of different shapes and/or configurations. In one form a heating element may be provided within the humidification tube.

While particular embodiments of this technology have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

The invention claimed is:

1. A humidifier configured to humidify a flow of breathable gas to be delivered to a patient's airways at a target humidity, the humidifier comprising:
   a heating element in the form of a resistance heater comprising a porous, electrically resistive material, the heating element being configured to be connected to an electrical power supply;
   a housing that encloses at least a portion of the heating element, the housing being formed of electrically insulating material configured to be electrically insulated from electrical energy supplied by the electrical power supply;
   a liquid water inlet configured to receive liquid water from a water supply unit, the liquid water inlet and the heating element being configured so that liquid water flowing through the liquid water inlet is conveyed through the porous, electrically resistive material; and
   a controller configured to:
      determine an ambient humidity;
      calculate an amount of liquid water to be supplied to the porous, electrically resistive material based on the determined ambient humidity and the target humidity;
      calculate an amount of energy required to vaporise the calculated amount of liquid water;
      control the water supply unit to deliver the amount of liquid water to the porous, electrically resistive material; and
      energise the heating element with the calculated amount of energy,
   wherein the housing is configured to retain the liquid water within the porous, electrically resistive material of the heating element.

2. The humidifier of claim 1, wherein the controller is further configured to control the water supply unit and the electrical power supply to deliver the vaporised water to the flow of breathable gas only during a portion of a patient's breathing cycle.

3. The humidifier of claim 2, wherein the portion of the patient's breathing cycle is an inspiratory phase.

4. The humidifier of claim 1, wherein the controller is configured to determine the ambient humidity as an absolute humidity.

5. The humidifier of claim 1, wherein the target humidity is an absolute humidity.

6. The humidifier of claim 1, wherein the controller is further configured to calculate the amount of liquid water to be provided to the porous, electrically resistive material based on a flow rate of the flow of breathable gas.

7. The humidifier of claim 1, wherein the housing comprises an inlet opening at a first end and an outlet opening at a second end that is opposite the first end, wherein the liquid water inlet is located at the inlet opening of the housing, and wherein the outlet opening is configured to discharge the vaporised water to the flow of breathable gas.

8. The humidifier of claim 1, wherein the porous, electrically resistive material comprises pores large enough to allow liquid water to flow through the porous, electrically resistive material.

9. The humidifier of claim 1, wherein the porous, electrically resistive material is configured so that the liquid water infiltrates the porous, electrically resistive material.

10. The humidifier of claim 1, wherein the housing that encloses at least a portion of the heating element is configured to isolate said at least a portion of the porous, electrically resistive material from the flow of breathable gas from the flow of breathable gas.

11. The humidifier of claim 1, further comprising the water supply unit.

12. The humidifier of claim 1, further comprising:
a first electrical connector that is located at a first end of the porous, electrically resistive material and is configured to be connected to the electrical power supply; and
a second electrical connector that is located at a second end of the porous, electrically resistive material and is configured to be connected to the electrical power supply,
wherein the housing is electrically insulated from the first and second electrical connectors.

13. The humidifier of claim 1, wherein the heating element extends beyond the housing so that the heating element is exposed to a space outside of the housing.

14. A respiratory apparatus comprising:
the humidifier of claim 1;
a flow generator for pressurizing the flow of breathable gas to be humidified; and
a patient interface to deliver humidified the flow of gas to the patient.

15. A humidifier configured to humidity a flow of breathable gas to be delivered to a patient's airways at a target humidity, the humidifier comprising:
a heating element in the form of a resistance heater comprising a porous, electrically resistive material, the heating element being configured to receive electrical power from a power supply;
a housing that encloses at least a portion of the heating element, the housing being formed of electrically insulating material configured to insulate the housing from the electrical power supplied from the power supply;
a liquid water inlet configured to receive liquid water from a water supply unit, the liquid water inlet and the heating element being configured so that liquid water flowing through the liquid water inlet is conveyed through the porous, electrically resistive material; and
a controller configured to:
determine an ambient humidity;
calculate a flow rate for supplying liquid water to the porous, electrically resistive material based on the determined ambient humidity and the target humidity;
calculate an amount of energy required to vaporise the liquid water flowing at the calculated flow rate;
control the water supply unit to deliver liquid water to the porous, electrically resistive material at the calculated flow rate; and
energise the heating element with the calculated amount of energy,
wherein the housing is configured to retain the liquid water within the porous, electrically resistive material of the heating element.

16. The humidifier of claim 15, wherein the controller is further configured to control the water supply unit and the power supply to deliver the vaporised water to the flow of breathable gas only during a portion of a patient's breathing cycle.

17. The humidifier of claim 16, wherein the portion of the patient's breathing cycle is an inspiratory phase.

18. The humidifier of claim 15, wherein the controller is configured to determine the ambient humidity as an absolute humidity.

19. The humidifier of claim 15, wherein the target humidity is an absolute humidity.

20. The humidifier of claim 15, wherein the controller is further configured to calculate the flow rate of the liquid water based on a flow rate of the flow of breathable gas.

21. The humidifier of claim 15, further comprising the water supply unit.

22. The humidifier of claim 15, further comprising:
a first electrical connector located at a first end of the porous, electrically resistive material and configured to be connected to the power supply; and
a second electrical connector located at a second end of the porous, electrically resistive material and configured to be connected to the power supply,
wherein the housing is electrically insulated from the first and second electrical connectors.

23. A humidifier configured to humidify a flow of breathable gas to be delivered to a patient's airways at a target humidity, the humidifier comprising:
a heating element in the form of a resistance heater comprising a porous, electrically resistive material, the heating element being configured to receive electrical power from a power supply;
a housing that encloses at least a portion of the heating element, the housing being formed of electrically insulating material configured to be electrically insulated from the electrical power supplied by the power supply;
a liquid water inlet configured to receive liquid water from a pump, the liquid water inlet and the heating element being configured so that liquid water flowing through the liquid water inlet is conveyed through the porous, electrically resistive material; and
a controller configured to:
determine an ambient humidity;
calculate a flow rate for supplying liquid water to the porous, electrically resistive material based on the determined ambient humidity and the target humidity;
calculate an amount of energy required to vaporize the liquid water flowing at the calculated flow rate;
control the pump to deliver liquid water to the porous, electrically resistive material at the calculated flow rate; and
energise the heating element with the calculated amount of energy,
wherein the housing is configured to retain the liquid water within the porous, electrically resistive material of the heating element.

24. The humidifier of claim 23, further comprising:
a first electrical connector located at a first end of the porous, electrically resistive material and configured to be connected to the power supply; and
a second electrical connector located at a second end of the porous, electrically resistive material and configured to be connected to the power supply,
wherein the housing is electrically insulated from the first and second electrical connectors.

25. The humidifier of claim 15, wherein a portion of the heating element is uncovered by the housing.

26. A respiratory apparatus comprising:
the humidifier of claim 15;

a flow generator for pressurizing the flow of breathable gas to be humidified; and a patient interface to deliver humidified the flow of gas to the patient.

27. The humidifier of claim 23, further comprising the pump.

28. The humidifier of claim 23, wherein the controller is further configured to control the pump and the power supply to deliver the vaporised water to the flow of breathable gas only during a portion of a patient's breathing cycle.

29. The humidifier of claim 28, wherein the portion of the patient's breathing cycle is an inspiratory phase.

30. The humidifier of claim 23, wherein the controller is configured to determine the ambient humidity as an absolute humidity.

31. The humidifier of claim 23, wherein the target humidity is an absolute humidity.

32. The humidifier of claim 23, wherein the controller is further configured to calculate the flow rate of the liquid water based on a flow rate of the flow of breathable gas.

33. The humidifier of claim 23, wherein the housing includes an opening through which the heating element is exposed to a space outside the housing.

34. A respiratory apparatus comprising:

the humidifier of claim 23;

a flow generator for pressurizing the flow of breathable gas to be humidified; and a patient interface to deliver humidified the flow of gas to the patient.

* * * * *

UNITED STATES PATENT AND TRADEMARK OFFICE
CERTIFICATE OF CORRECTION

PATENT NO. : 11,744,979 B2  
APPLICATION NO. : 16/390808  
DATED : September 5, 2023  
INVENTOR(S) : Roger Mervin Lloyd Foote Page 1 of 1

It is certified that error appears in the above-identified patent and that said Letters Patent is hereby corrected as shown below:

In the Claims

In Claim 15, Column 23, Line 31, "A humidifier configured to humidity a flow of breath-able" should read -- A humidifier configured to humidify a flow of breath-able --.

Signed and Sealed this  
Third Day of October, 2023

Katherine Kelly Vidal  
*Director of the United States Patent and Trademark Office*